(12) United States Patent
Li et al.

(10) Patent No.: US 7,794,959 B2
(45) Date of Patent: Sep. 14, 2010

(54) IDENTIFICATION OF BITTER RECEPTORS FOR HYDROLYZED SOY PROTEIN

(75) Inventors: Xiaodong Li, San Diego, CA (US); Hong Xu, San Diego, CA (US); Lan Zhang, San Diego, CA (US); Hanghui Liu, San Diego, CA (US); Keping Wu, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

(21) Appl. No.: 12/053,855

(22) Filed: Mar. 24, 2008

(65) Prior Publication Data

US 2009/0074894 A1   Mar. 19, 2009

Related U.S. Application Data

(60) Continuation-in-part of application No. 11/766,974, filed on Jun. 22, 2007, and a continuation-in-part of application No. 11/555,617, filed on Nov. 1, 2006, and a division of application No. 10/724,209, filed on Dec. 1, 2003, now Pat. No. 7,393,654, and a continuation-in-part of application No. 10/191,058, filed on Jul. 10, 2002, now Pat. No. 7,338,771.

(51) Int. Cl.
G01N 33/567 (2006.01)
C07K 14/705 (2006.01)

(52) U.S. Cl. .................. 435/7.21; 435/7.2; 436/501

(58) Field of Classification Search .................. None
See application file for complete search history.

(56) References Cited

U.S. PATENT DOCUMENTS

| | | |
|---|---|---|
| 2002/0051997 A1 | 5/2002 | Zucker et al. |
| 2004/0214239 A1 | 10/2004 | Servant et al. |
| 2005/0084506 A1 | 4/2005 | Tachdjian et al. |
| 2007/0172579 A1 | 7/2007 | Blanton et al. |
| 2008/0038739 A1 | 2/2008 | Li et al. |

*Primary Examiner*—John D Ulm
(74) *Attorney, Agent, or Firm*—Hunton & Williams LLP

(57) ABSTRACT

The present invention relates to the discovery that specific human taste receptors in the T2R taste receptor family respond to particular bitter compounds present in hydrolyzed soy protein derived materials. The invention further relates to the use of these T2R receptors in assays for identifying ligands that modulate the activation of these taste receptors by specific bitter ligands present in hydrolyzed soy protein materials and derivatives thereof and related compounds. These compounds may be used as additives and/or removed from soy-based foods, beverages, cosmetics and medicinals in order to modify (block) T2R-associated bitter taste elicited by bitter ligands present in hydrolyzed soy protein materials. Also these T2R ligands potentially may be used as therapeutics to treat and modulate hT2R1 or hT2R67 associated gastrointestinal and metabolic functions such as serum cholesterol levels as well as treat gastrointestinal and metabolic diseases such as eating disorders, food sensing, food absorption, obesity, diabetes, Crohn's disease, celiac disease, et al.

25 Claims, 8 Drawing Sheets

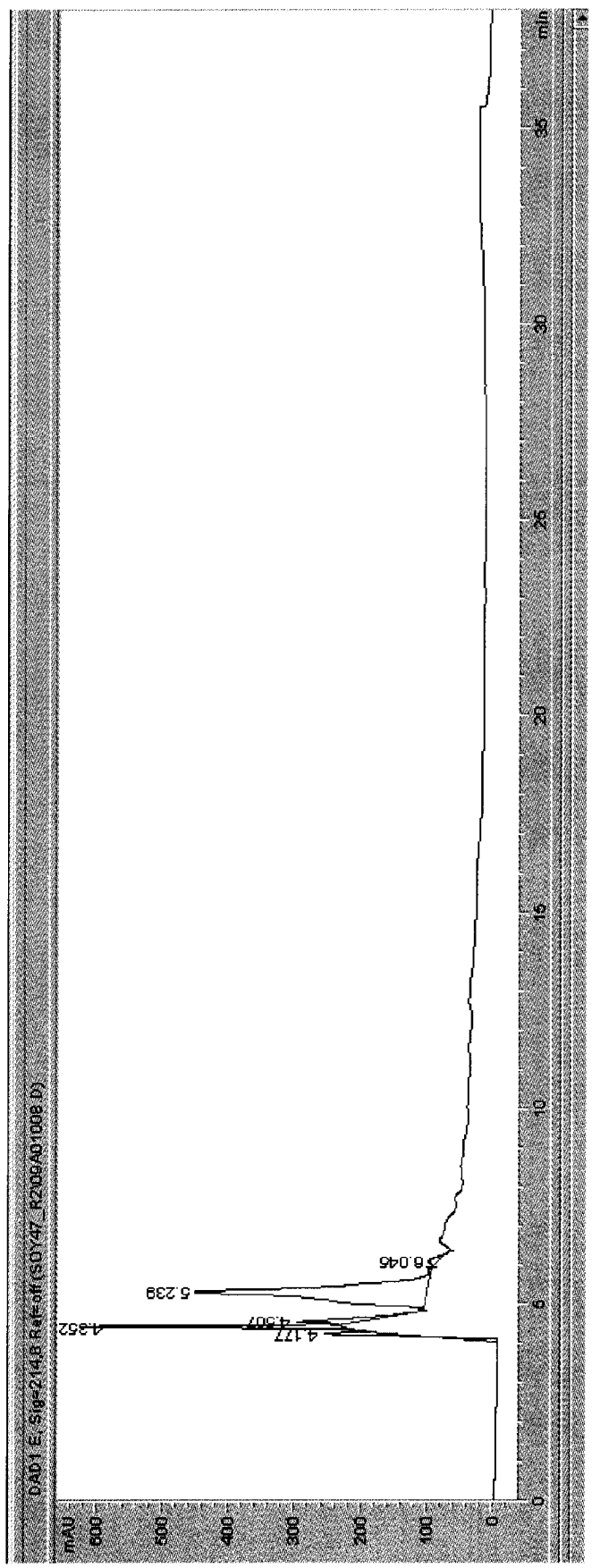
FIG. 1A Fractionation of hydrolyzed soy protein

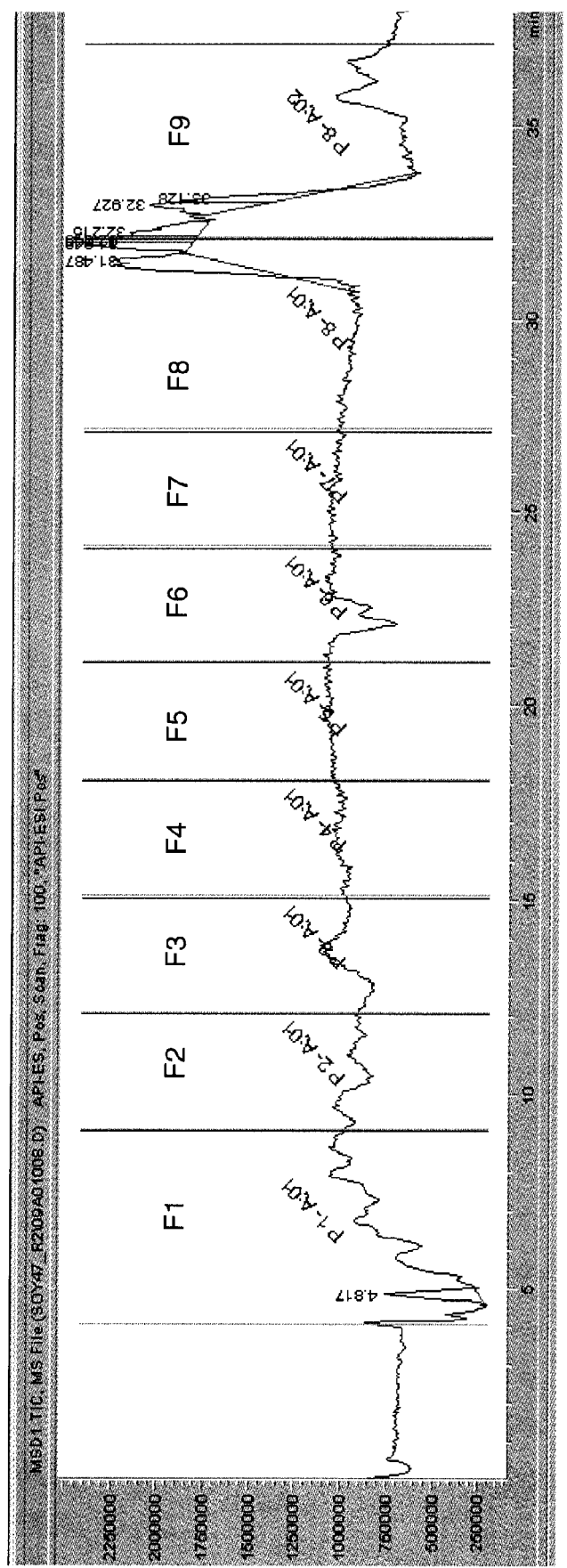
FIG. 1B Fractionation of hydrolyzed soy protein

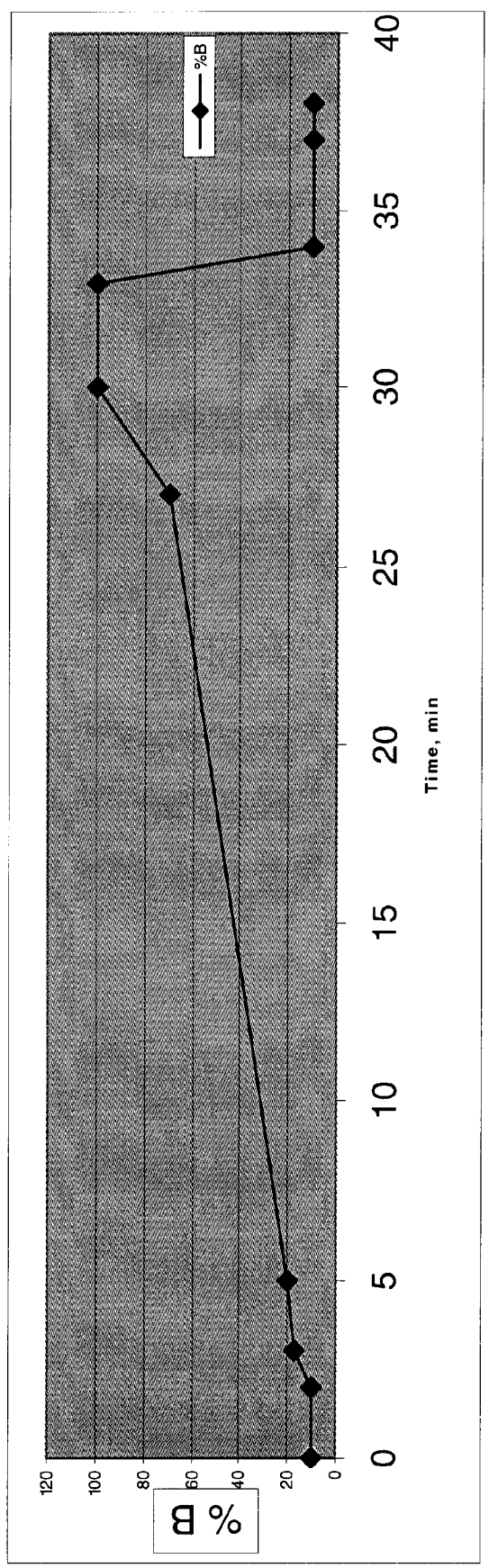
FIG. 1C Fractionation of hydrolyzed soy protein

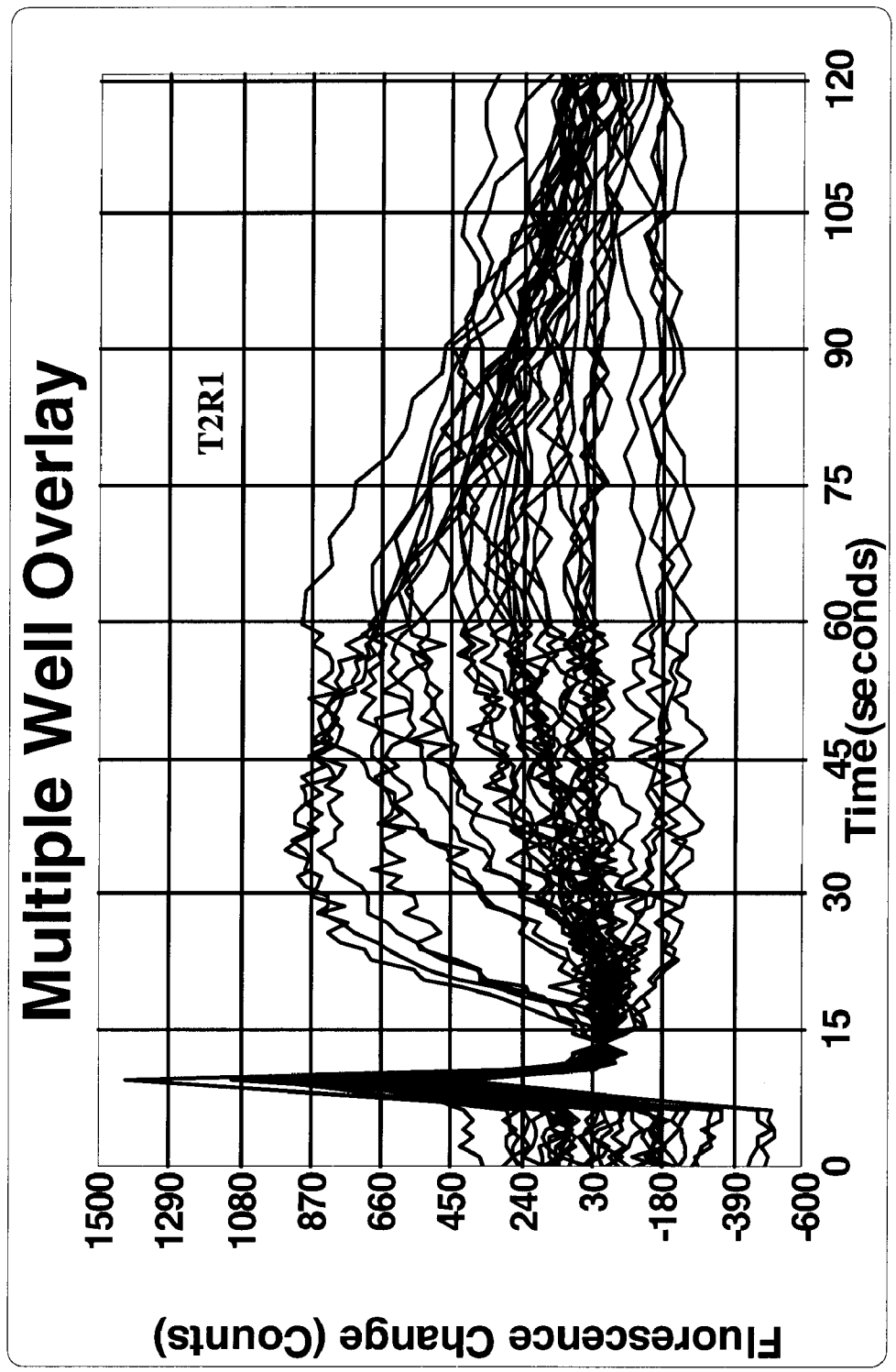
FIG. 2A Human T2R1 and 67 responded to soy protein fraction 3

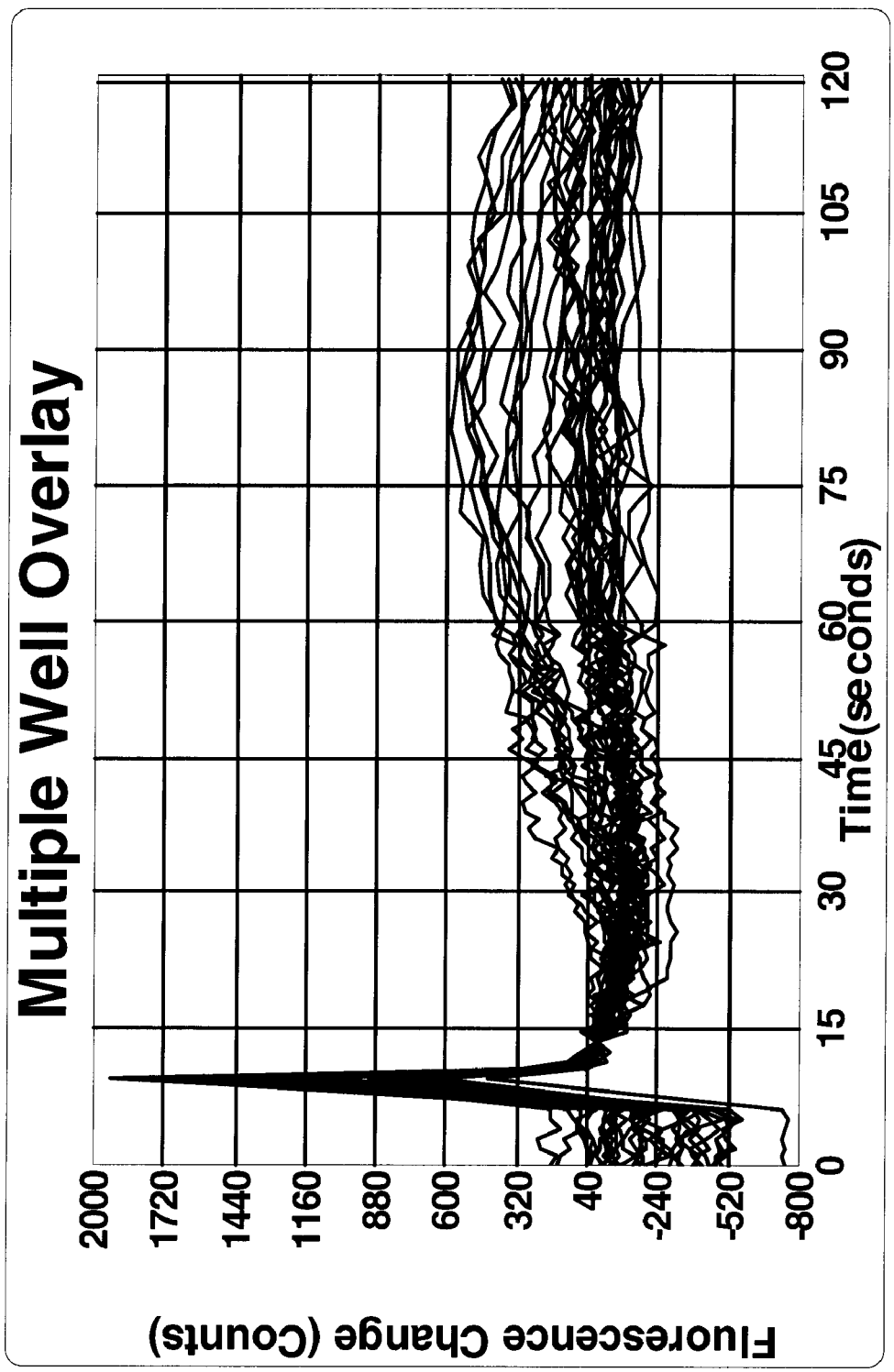
FIG. 2B Human T2R1 and 67 responded to soy protein fraction 3

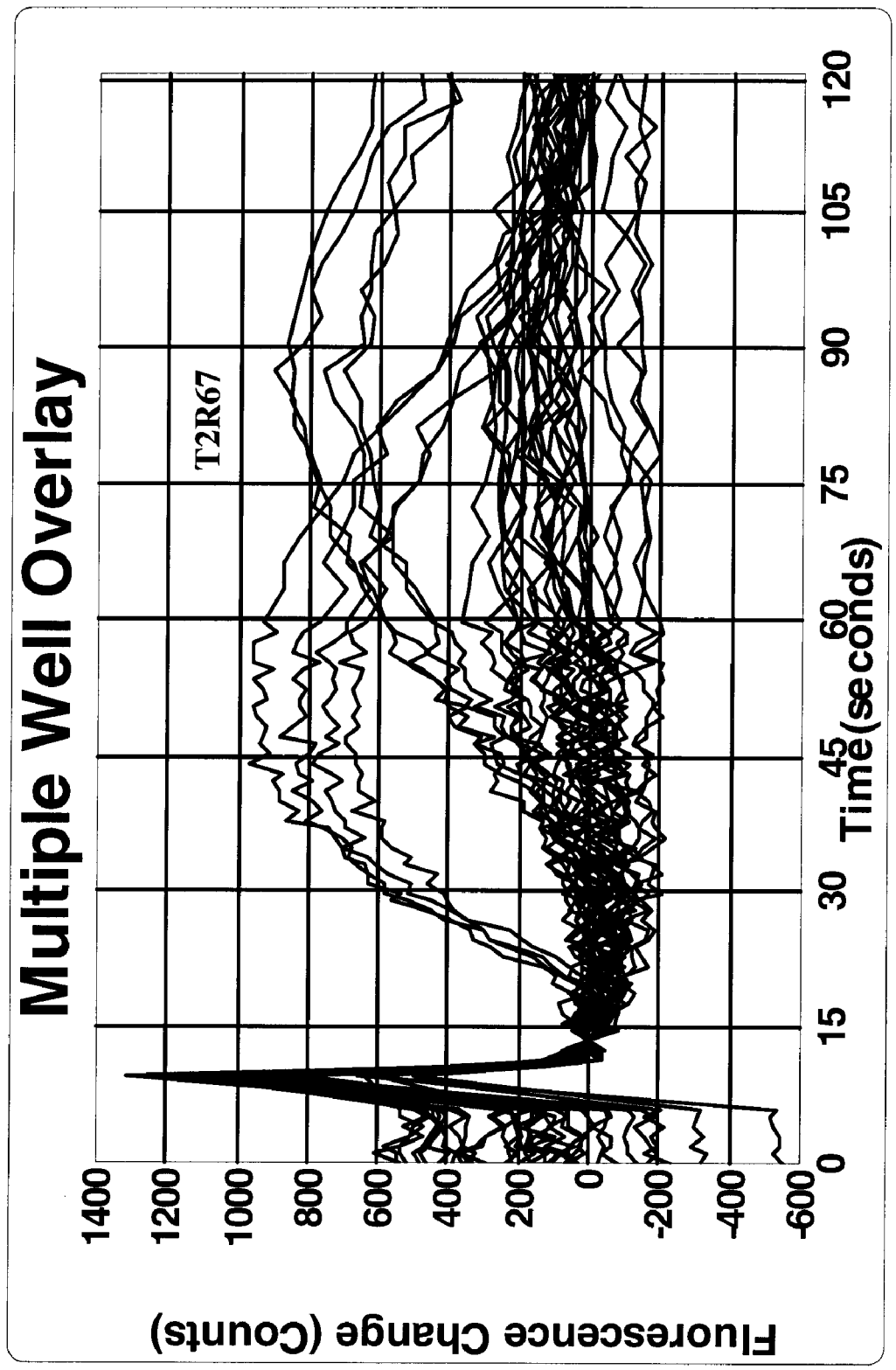
FIG. 2C Human T2R1 and 67 responded to soy protein fraction 3

Figure 3 hT2R1 stable cell lines (showing 4 clones and control cell line without hT2R1) responding to methylthiourea
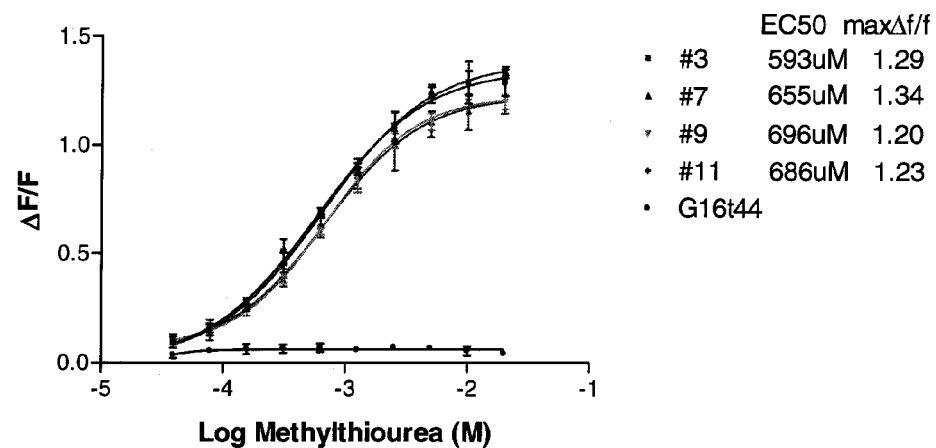

Figure 4 hT2R67 stable cell lines (showing 4 clones and control cell line without hT2R1) responding to andrographolide
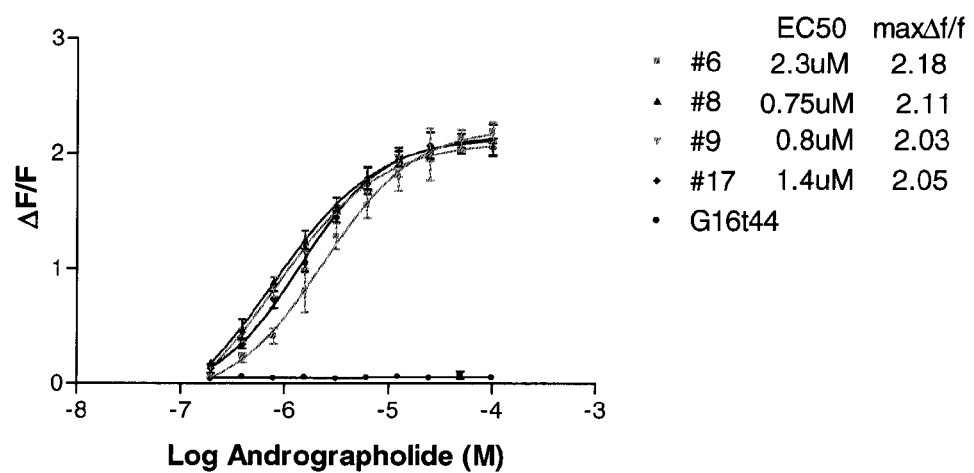

US 7,794,959 B2

IDENTIFICATION OF BITTER RECEPTORS FOR HYDROLYZED SOY PROTEIN

RELATED APPLICATIONS

This application is a continuation-in-part of U.S. Ser. No. 11/766,974 filed on Jun. 22, 2007, and relates to earlier applications by the present assignee Senomyx Inc. describing human T2R (bitter) taste receptors and the use thereof in screening assays including in particular U.S. Ser. No. 11/766,974 which is a continuation-in-part of U.S. Ser. No. 11/555,617 filed on Nov. 1, 2006, which is itself a continuation-in-part of U.S. Ser. No. 10/191,058 filed Jul. 10, 2002 (now U.S. Pat. No. 7,338,771) and is also a continuation-in-part of U.S. Ser. No. 10/724,209 filed on Dec. 1, 2003 (now U.S. Pat. No. 7,393,654), which is a divisional of U.S. Ser. No. 09/825,882 filed on Apr. 5, 2001, now U.S. Pat. No. 7,105,650 all of which applications are incorporated by reference in their entireties herein. These applications relate to the cloning of hT2Rs and disclose the amino acid and DNA sequences thereof and further describe the use thereof in assays for the identification of ligands that activate specific T2Rs. These ligands are useful for modulating taste perception, particularly bitter taste.

SEQUENCE LISTING

The sequence listing in the file named "67824o730001.txt" having a size of 11857 bytes that was created Nov. 4, 2008 is hereby incorporated by reference in its entirety.

FIELD OF THE INVENTION

The present invention generally relates to the elucidation of human T2R taste receptors that functionally respond to bitter ligands comprised in hydrolyzed soy proteins and the use of these receptors in assays to identify compounds that may be used as flavor additives which function to reduce the bitter taste of consumable products containing hydrolyzed soy protein materials or to improve the taste of other foods and beverages containing bitter compounds comprised in hydrolyzed soy protein materials.

More specifically, the invention relates to the discovery that hT2R1 and hT2R67 both functionally respond to one or more bitter tasting compounds or complexes comprised in hydrolyzed soy protein compositions.

Also, based on this discovery the present invention relates to the use of hT2R1 and/or hT2R67 or fragments, or variants or chimeras thereof, including orthologs, splice variants, single nucleotide polymorphisms (SNPS), and genetically engineered mutants thereof including those produced by combining or substituting the ligand binding residues or binding domains of hT2R1 or hT2R67 with the corresponding domains or residues of other human or non-human T2Rs or other GPCR's in assays, preferably high throughput cell-based assays, for identifying compounds that modulate (preferably block) the bitter taste of bitter compounds present in hydrolyzed soy protein compositions, as well as structurally related compounds or other bitter compounds that activate these receptors and thereby elicit an undesired bitter taste. Compounds identified using these assays may be used as flavor additives in foods, beverages or medicinal products to improve the taste thereof, especially soy based products. In addition, these compounds may be used as flavor additives in other consumables similarly containing bitter compounds that are comprised in hydrolyzed soy products. Additionally, the invention relates to modified foods, beverages and medicinals that are treated and formulated in order to reduce or eliminate the bitter taste elicited by compounds that activate the subject T2Rs.

Also, the present invention relates to the use of the subject T2R genes and the corresponding polypeptides and cells which express same in therapeutic screens, e.g., for identifying compounds that can be used to modulate gastrointestinal functions such as food sensing, absorption, regulation of gastrointestinal hormone and peptide secretion, transport and absorption, responses to toxins in the lingual and gastrointestinal systems, treatment of gastrointestinal and metabolic disorders such as eating disorders, diabetes, obesity, and the like. In particular because soy compositions contain compounds that are known to promote the reduction of serum cholesterol compounds that modulate the activation of hT2Rs by compounds present in soy may also have a beneficial effect on serum cholesterol levels.

DESCRIPTION OF THE RELATED ART

Soy provides an inexpensive and healthy source of dietary protein. It is well known that vegetable products, such as soy protein products, contain no cholesterol. For decades, nutritional studies have indicated that the inclusion of soy protein in the diet reduces serum cholesterol levels. Based thereof, a number of foods and drink products available today utilize soy protein isolates including, for example, dry blended beverages, ready to drink beverages that are of neutral or acidic pH, yogurt, dairy products, breads, food and protein bars, cereal products, soups, gravies, infant formula, emulsified meat products, whole muscle meat products, ground meat products other meat products such as beef, pork, poultry, and seafood, meat analogs, and the like. Also, soy milk is widely used in different beverages and is ingested especially by persons with allergies or adverse reactions to dairy products.

Despite all of the above advantages that soy proteins provide, it is well known that by supplementing foods with increased levels of dietary fiber and soy proteins, taste can be seriously compromised and that such materials may possess and undesired bitter taste. More particularly, protein sources, such as soy protein, especially in hydrolyzed form, can produce objectionable off-flavors in the finished products.

In particular it has been reported by Cho et al., of the Solae Company in J Agric Food Chem. 2004 Sep. 22; 52(19):5895-901 that the hydrolysis of soy proteins produce different bitter peptides, which are probably the major source of bitter off taste and further describe the hydrophobicity of bitter peptides from soy protein hydrolysates. More particularly, Cho et al. (Id.) teach the characterization of various soy peptides for flavor, chemical properties, and hydrophobicity to investigate their relationships with bitterness. Five peptide fractions ranging in average molecular mass from 580 to 11300 Da were fractionated by ultrafiltration from two commercial soy protein hydrolysates. The bitterness of fractionated peptides was related to molecular mass, with maximum bitterness observed at approximately 4000 Da for one hydrolysate and 2000 Da for the other. The bitterness increased as the peptide M(w) decreased to 3000 Da for the first hydrolysate and to 2000 Da for the second one and then decreased as the peptide M(w) decreased below 1000 Da. The peptide fraction with molecular mass of <1000 Da showed the lowest bitterness for both. Therefore, these peptides are believed to be largely responsible for the bitter taste of some hydrolyzed soy protein materials.

Related thereto, many consumers complain that high protein foods, like those supplemented with soy protein, taste grassy, beany, or bitter. Soy off-flavors may be responsible for most of the complaints with respect to the taste of soy-based products. While peptides are believed to be the prevalent cause of the bitter after taste of hydrolyzed soy protein derived materials, it has further been reported that the development of soy off-flavors can be initiated when phospholipids and triglycerides undergo hydrolysis to yield polyunsaturated free fatty acids, which then react with molecular oxygen to form fatty acid hydroperoxides and other oxygenated lipid species. Both the hydrolysis and the oxidation can occur in enzyme-catalyzed and in non-enzyme-catalyzed reactions. The hydroperoxides then decompose into smaller molecules such as aldehydes and ketones and it is these small molecules that are responsible for the odor and flavor of vegetable oil-based products. In particular, Boatwright (U.S. Pat. No. 6,426,112), Boatwright et al., J. Food Sci. Vol 66, page 1306 (2001), Boatwright et al., J. Food Sci. Vol 65, page 819 (2000), Y. Feng, et al. (Aroma Active Compounds in Food, ACS Symposium Series 794, ed. G. R. Takeaka et al., page 251 (2001)), and A. Kobayashi et al. (J. Agric. Food Chem., vol. 43, page 2449 (1995)) have identified some of the most flavor active of these molecules in soy isolate and soymilk, which contribute to soy protein's unique flavor. Specifically, these molecules may include methanethiol, dimethyl trisulfide, 2-pentyl pyridine, (E,E)2,4-nonadienal, (E,Z)2,6-nonadienal, (E,E)2,4-decadienal, (E,Z)2,4 decadienal, acetophenone, hexanal, 1-octen-3-one, beta-damascenone, (E)2-nonenal, (E)4,5-epoxy-(E)-2-decenal, vanillin, maltol, 1-octen-3-ol, 2-pentyl furan, 2-heptanone, octanal, (E)3-octen-2-one, 2-decanone, benzaldehyde, dimethyl disulfide, and 2,3-butanedione. Most of these flavor active volatiles are derived from oxidation of polyunsaturated lipids. The formation of these flavor active molecules and their hydroperoxide precursors begins as soon as the bean is crushed and continues through the soy isolate manufacturing process. Traditional processing methods have not been completely successful in reducing the level of off-flavors and off-flavor precursors to an acceptable level in finished soy isolate or in foods to which it is added. In particular, a problem exists with the bitterness of hydrolyzed soy protein containing compositions which are used in many comestibles, believed to be largely attributable to the presence of bitter peptides produced during the hydrolysis processing procedures.

The conventional process for manufacturing soy protein isolate begins with the production of a full fat soy flake from the bean, which is substantially defatted with hexane. This process typically removes more than 80% of the acid hydrolysable lipids in the soy flake, as measured by AOAC Method 922.06. The majority of the lipids remaining in the extracted flake are phospholipids. Soy protein is then extracted from the defatted soy flour with water and separated from the insoluble vegetable matter using centrifugation. The extracted protein is precipitated, washed, re-suspended in water and spray dried as described, for example, in Hettiarachchy, et al., Soybeans: Chemistry, Technology, and Utilization, pp. 379-411, Aspen Publishers (1997), which is incorporated herein by reference in its entirety.

In general products and fractions which may be derived from soy may include by way of example soy milks, soy oils, and soy lecithin as well as defatted soy flakes which may be used to produce soy flours, soy protein concentrates and soy protein isolates. As is well known in the art soymilk is the liquid remaining after straining soybeans that have been soaked, ground and then cooked. Soy lecithin is the combination of phospholipids that naturally occurs in soybeans and is obtained after the soy oil has been extracted from soybean flakes. Soy flours are derived by grinding dehulled, defatted soybean flakes and is about 50% protein and further contains carbohydrate components of the soybean sugars, oligosaccharides and fibers. Soy protein concentrates are produced by removing a portion of the carbohydrates from defatted, dehulled soybeans. These concentrates comprise fiber and are typically at least 65% protein calculated on a moisture free basis. Soy protein isolates are prepared by water extraction and moderate heating of soy flakes and are typically at least 90% protein by dry weight.

These processes have been generally unsuccessful in producing a soy protein isolate with an acceptable flavor in addition to the presence of bitter peptides, possibly because the hexane is inefficient at removing all of the phospholipids and triglycerides that contain polyunsaturated fatty acids; low levels of these off-flavor precursors, and some of the enzymes which act on them, remain after the hexane extraction. Therefore, these components may continue to generate off-flavors during the removal of hexane from the extracted soy flake at elevated temperatures. Appreciable quantities of the flavor-active volatiles are also present and may continue through the subsequent protein isolation steps resulting in a soy protein isolate with the familiar grassy, or beany flavor.

In addition to the volatile compounds mentioned above, isoflavones occur naturally in soybeans. Isoflavone compounds include daidzin, 6"-O-malonyldaidzin, 6"-O-acetyldaidzin, daidzein, genistin, 6"-O-malonylgenistin, 6"-O-acetylgenistin, genistein, glycitin, 6"-O-malonylglycitin, and glycitein. The isoflavone compounds are associated with the inherent bitter flavor of soybeans, and isolates produced therefrom. Additionally, it has been recognized that potassium, which is also present in soybeans and products derived therefrom, may also contribute to the bitter off-flavors of soy protein products and isolates.

In the case of hydrolyzed soy proteins, as mentioned above, and disclosed by Cho et al. (Id.) current research indicates that the prevalent cause of bitterness thereof is the presence of one or more peptides that elicit a bitter after-taste on ingestion.

As is evident from the foregoing, a need exists in the industry for soy protein products with high functionality that have improved flavor characteristics, especially a reduced bitter taste. Additionally, a need exists for processing methods for making these isolates, especially those containing hydrolyzed soy proteins.

Relating to this objective, bitter taste in humans and the specific receptors and ion channels involved in eliciting bitter taste has recently become more understood. One of the basic taste modalities that humans can recognize is bitter. It is now known that many bitter compounds produce bitter taste by interacting with cell surface receptors. These receptors belong to the family of seven transmembrane domain receptors that interact with intracellular G proteins. A novel family of GPCRs, termed T2Rs, has been identified in humans and rodents (Adler et al., Cell 100(6):693-702 (2000); Chandrashekar et al., Cell 100(6): 703-711 (2000); Matsunami H, Montmayeur J P, Buck L B. Nature 404(6778): 601-4 (2000 Sequences of hT2Rs have been previously reported and are disclosed in published PCT applications by Zuker et al. (WO 01/18050 A2, (2001)) and Adler et al. (WO 01/77676 A1 (2001)) as well as the Senomyx applications identified supra all of which are incorporated by reference in their entirety herein.

Specifically, in Applicants' earlier patent application, U.S. Ser. No. 09/825,882, now patented, Applicants identified and provided the nucleic acid sequences and polypeptide sequences for a number of then-novel human taste receptors including hT2R51, hT2R54, hT2R55, hT2R61, hT2R63, hT2R64, hT2R65, hT2R67, hT2R71, and hT2R75. Additionally in U.S. Ser. No. 11/555,617 filed on Nov. 1, 2006 Applicants provided the polypeptide and DNA sequences for different human T2R taste receptors and further identify bitter ligands that induce the activation of these T2Rs. Also in U.S. Ser. No. 11/766,974 filed on Jun. 22, 2007 Applicants further identify other bitter ligands that specifically bind to these human T2Rs, and provide related assays.

Also, relating to practical utilities of the present invention it has been reported that T2Rs are expressed in the gastrointestinal system. For example, Wu et al., Proc, Natl. Acad. Sci, USA 99(4):2392-7 (2002) report that T2Rs are expressed in enterendocrine cells (STC1 cells) as well as gustducin and transducin subunits and that these cells likely respond to bitter ligands in the gastrointestinal tract. Also, it has been reported by Chen et al., AM J. Physiol. Cell Physiol. 291(4):C726-39 (2006) that bitter taste stimuli induce Ca++ signaling and cholecystokinin (CCK) release in enterendocrine STC-1 cells. Also, Rozengurt, A J Physiology Gastrointestinal Liver Physiol 291(2):G171-7 (2006) report that taste receptors in the gut likely play a role in molecular sending the control of digestive functions, and hormonal and/or neutronal pathways and that they may play a role in the detection of harmful drugs and survival responses. Further, Stermini Am J Physiol Gastrointest Liver Physiol. 292(2):G457-61 (2007) report that taste receptors in the gut may be involved in gastrointestinal functions such as molecular sensing, nutrient absorption, protection from harmful substances, and further suggest that an understanding of these mechanisms may be relevant to disease states and conditions such as feeding disorders, and inflammation. Further, it has been recently suggested by Mace et al., J. Physiol. 2007 [Epub] that T2Rs and T1Rs activate phospholipase C beta 2, PLC beta2, and that there is likely a molecular intestinal sensing system in the gut similar to that present in lingual cells and that gastrointestinal cells such as brush cells or solitary chemosensory cells expressing taste receptors may result in GLUT2 increase and may play a role in nutrient sensing, and nutrition in the treatment of obesity and diabetes.

However, notwithstanding what has been reported and the understanding that T2R members regulate bitter taste, and their possible role in gastrointestinal functions and taste there exists a need for the identification of specific ligands which activate human bitter T2R taste receptors. A greater understanding of the binding properties of different T2Rs, particularly human T2Rs, would be highly beneficial as it will greater facilitate the use thereof in selecting compounds having desired taste modulatory properties, i.e., which block or inhibit the taste of specific bitter compounds, especially bitter peptides present in compositions containing hydrolyzed soy proteins or other ingestible compositions. Also, it will provide for the identification of compounds for treating and modulating gastrointestinal functions and related diseases involving hT2R1 or hT2R67 activation such as obesity, diabetes, food absorption, food sensing, eating disorders, and in the regulation of related hormones and peptides such as GLUT2, cholecystokin et al.

SUMMARY OF THE INVENTION

Toward that end, the present invention relates to the discovery of human taste receptors in the T2R family, particularly hT2R1 and hT2R67 that specifically bind and/or functionally respond to bitter ligands comprised in soy, especially hydrolyzed soy protein compositions.

More specifically, the present invention relates to assays for identifying compounds that block or inhibit the bitter taste of hydrolyzed soy proteins and bitter ligands contained therein, most especially bitter peptides that are produced when soy proteins are hydrolyzed.

Also the present invention identifies specific bitter fractionated extracts comprised in soy and bitter compounds contained therein which may comprise bitter peptides, which activate the hT2R1 and hT2R67 taste receptors.

Also, the present invention provides assays, preferably high throughput screening assays for identifying compounds that modulate the activation of hT2R1 and/or hT2R67 by bitter compounds that are present in soy, particularly hydrolyzed soy protein containing compositions, and other consumable products. As mentioned these bitter compounds include in particular various bitter peptides, including hydrophobic peptides present in hydrolyzed soy protein containing compositions.

These discoveries were made using cell-based assays that measured the activity of T2Rs using cells that express a particular T2R in the presence and absence of specific bitter ligands. In particular, as described in greater detail infra, HEK cell lines expressing the above-identified and other T2Rs on their surface and which further expressed a chimeric G protein that functionally couple to said T2Rs were used in cell-based assays that detected changes in intracellular calcium concentrations, and were found to be specifically activated by specific bitter compounds found in soy whereas other hT2Rs were not activated under similar conditions.

Therefore, the invention embraces the use of these human taste receptors in assays, preferably high-throughput assays, to identify compounds that modulate, preferably block, the activation of these receptors by these and other bitter compounds found in soy containing products, especially those containing hydrolyzed soy protein containing materials.

Also, the invention relates to the use of these receptors to identify compounds present in hydrolyzed soy proteins and related hydrolyzed vegetable proteins that elicit bitter taste.

Also, the present invention relates to the use of the subject T2Rs and corresponding polypeptides and cells which express same in therapeutic screening assays, e.g., for identifying compounds that regulate or modulate gastrointestinal functions such as food and nutrient sensing, food absorption, regulation of digestive hormones and peptides, responses to toxins, and for treating gastrointestinal or metabolic diseases such as obesity, diabetes, and inflammatory or autoimmune gastrointestinal diseases such as IBD, celiac disease, Crohn's disease, et al. As mentioned, compounds which modulate the activation of hT2R1 or hT2R67 by soy derived products may have a beneficial effect on serum cholesterol levels.

The invention also embraces assays which include an additional step which evaluates the effect of the identified modulating compounds in human or other taste tests, and evaluates the effect of the identified compounds on bitter taste and/or in further in vitro or in vivo clinical tests to evaluate the effect of an identified compound on a specific gastrointestinal, digestive or metabolic function or disease such as its effect on serum cholesterol.

Also, the invention preferably embraces the use of the identified compounds in foods, beverages and medicines as flavor or taste modulators, i.e., to inhibit bitter taste, e.g., the bitter taste associated with specific beverages and foods or medicaments containing hydrolyzed soy proteins or bitter ligands present therein, especially bitter peptides produced during the hydrolysis of soy proteins.

These compounds may be used in any comestible containing soy proteins, especially hydrolyzed soy proteins or containing bitter ligands present therein. This includes comestibles for human and animal consumption. Examples thereof which are identified for illustrative purposes include by way of example, energy bars and gels; nutrition bars; meal replacements; dietary supplements; vitamins; non-dairy beverages/soymilk; meat alternatives (soy based); chips & snacks; tofu; dressings and condiments; frozen foods; ready meals; canned/preserved food; dried processed food; food supplements; cheese & cheese alternatives; soup, entrees & mixes; yogurt & kefir/soy yogurt & kefir; cookies & snack bars; cold cereals; baking mixes, supplies & flours (e.g. soy flour); confectionery; frozen fruits & vegetables (e.g. frozen green soybeans); bread & baked goods (frozen & non frozen); sauces, salsas & dips; pastas; puddings & desserts; herbal formulas; juices & functional drinks; seasonings; soynuts & mixes; packaged fresh produce; coffee, coffee substitutes & cocoa; hot cereals; beans, grains & rice; carbonated beverages and other drinks; spreads, conserves, jams & nut butters/soynut butter; baked goods; dairy products and dairy alternatives; baby food/infant formula; chilled processed food; ice cream and frozen yogurt (including soy based); and clinical nutrition products.

In addition, the subject invention embraces any comestible, including animal feeds or pet foods containing such compounds including by way of example the use thereof in soy containing dog, bird, and cat food compositions, animal feeds for consumption by cattle, horses, goats or other farm animals, and animal feed compositions for use in feeding zoo animals.

Further, the invention embraces the use of these compounds in pharmaceuticals and compositions for use in oral hygiene such as tooth pastes, mouth washes, dentifrices, and the like.

Further, the invention embraces the production of food, beverages and medicinals which have been treated to remove compounds that specifically activate bitter taste receptors, e.g., foods and beverages that have been processed to remove or reduce the amount of bitter compounds comprised therein such as bitter peptides that activate hT2R1 or hT2R67 in the subject assays.

Still further the present invention embraces medicaments containing identified compounds suitable for treating or preventing metabolic disorders, digestive functions, and gastrointestinal diseases involving T2Rs. Particularly, the present invention contemplates medicaments for treating or modulating conditions such as Crohn's, celiac disease, obesity, diabetes, food sensing, food absorption, digestive hormone or peptide secretion, and the like.

OBJECTS OF THE INVENTION

It is an object of the invention to provide assays that identify compounds which activate or which block or modulate the activation of hT2R1 or hT2R67 or fragments, variants, orthologs, or chimeras thereof by bitter ligands present in soy and other ingestibles, including the specific bitter ligands disclosed herein found in soy which specifically bind and activate these human bitter taste receptors.

It is a specific object of the invention to provide assays that identify compounds which activate or which block or modulate the activation and/or binding of hT2R1 or fragments, variants, or chimeras thereof by hydrolyzed soy and bitter compounds contained therein such as bitter peptides, present in hydrolyzed soy protein compositions and other bitter compounds such as methylthiourea and other ingestibles containing these same or structurally related or unrelated bitter compounds that activate hT2R1 or hT2R67.

It is another specific object of the invention to provide assays that identify compounds which activate or which block or modulate the activation and/or binding of hT2R67 or a fragment, ortholog, variant or chimera thereof by hydrolyzed soy and bitter compounds contained therein such as bitter peptides present in hydrolyzed soy protein compositions, andrographolide and other ingestibles containing these same or structurally related or unrelated bitter compounds.

It is a specific object of the invention to use cells or cell membranes that comprise or express (stably or transiently) at least one of hT2R1 or hT2R67 or a fragment, variant, ortholog, mutant or chimera thereof in assays to identify compounds present in hydrolyzed soy and other ingestibles that activate or which block or modulate the activation of at least one of said receptor by hydrolyzed soy or one of the above-identified bitter compounds or another structurally related bitter compound.

It is an even more specific object of the invention to use cells, preferably mammalian, amphibian or insect cells, e.g., HEK293T cells that express a G protein that couples thereto, e.g., $G_{\alpha 15}$, $G_{\alpha 16}$, gustducin or a chimera thereof, e.g., $G_{\alpha 16}$ gustducin or transducin chimeric G protein in cell-based assays that detect changes in intracellular calcium order to detect compounds that activate or which modulate, preferably block or inhibit, the activation of hT2R1 or hT2R67 by hydrolyzed soy or a bitter compound contained therein or by a related bitter compound.

It is another object of the invention to confirm that the identified compounds modulate, preferably inhibit or block, bitter taste, e.g. that elicited by hydrolyzed soy containing products, bitter compounds contained therein or other structurally related bitter compounds in human or animal taste tests, preferably human taste tests.

It is another object of the invention to utilize compounds identified in the assays described herein as additives or flavor modulators in compositions in order to inhibit or block the bitter taste elicited by hydrolyzed soy products and bitter compounds contained therein that specifically activate these taste receptors. A preferred object of the invention is to use a compound that inhibits activation of at least one of the above-identified human T2R receptors in a soy protein containing food, beverage or nutriceutical in order to block or inhibit the bitter taste thereof.

It is a specific object of the invention to use of the identified compounds in foods, beverages and medicines as flavor or taste modulators, i.e., to inhibit bitter taste, e.g., the bitter taste associated with specific beverages and foods or medicaments containing hydrolyzed soy proteins or bitter ligands present therein, especially bitter peptides and other compounds produced or retained during the hydrolysis of soy proteins.

It is a more specific object of the invention to use these compounds may be used in any comestible containing soy proteins, especially hydrolyzed soy proteins or containing bitter ligands present therein. This includes all comestibles suitable for human and animal consumption. Examples thereof which are identified herein for illustrative purposes include by way of example, energy bars and gels; nutrition bars; meal replacements; dietary supplements; vitamins; non-dairy beverages/soymilk; meat alternatives (soy based); chips & snacks; tofu; dressings and condiments; frozen foods; ready meals; canned/preserved food; dried processed food; food supplements; cheese & cheese alternatives; soup, entrees & mixes; yogurt & kefir/soy yogurt & kefir; cookies & snack bars; cold cereals; baking mixes, supplies & flours (e.g. soy flour); confectionery; frozen fruits & vegetables (e.g. frozen green soybeans); bread & baked goods (frozen & non frozen); sauces, salsas & dips; pastas; puddings & desserts; herbal formulas; juices & functional drinks; seasonings; soynuts & mixes; packaged fresh produce; coffee, coffee substitutes & cocoa; hot cereals; beans, grains & rice; carbonated beverages and other drinks; spreads, conserves, jams & nut butters/soynut butter; baked goods; dairy products and dairy alternatives; baby food/infant formula; chilled processed food; ice cream and frozen yogurt (including soy based); and clinical nutrition products.

In addition, it is another object of the invention to use the subject compounds as additives in animal feeds or pet foods containing soy proteins including by way of example the use thereof in soy containing dog, bird, and cat food compositions, animal feeds such as those for consumption by cattle, horses, goats or other farm or agricultural animals for food or non-food usage, and in animal feed compositions for use in feeding zoo animals.

Further, the invention embraces the use of these compounds in pharmaceuticals and compositions for use in oral hygiene such as tooth pastes, mouth washes, dentifrices, and the like.

Further, the invention embraces the production of food, beverages and medicinals which have been treated to remove compounds that specifically activate hT2R1 or hT2R67 bitter taste receptors, e.g., foods and beverages that have been processed to remove or reduce the amount of bitter compounds comprised therein such as bitter peptides that activate hT2R1 or hT2R67 which are identified using the subject assays.

DETAILED DESCRIPTION OF THE FIGURES

FIG. 1 FIGS. 1A-1C depict the fractionation of hydrolyzed soy protein into 9 different fractions designated F1 through F9.

FIG. 2 FIGS. 2A-2C contain the results of a calcium imaging assay that demonstrated that cell lines stably expressing hT2R1 or hT2R67 responded to a hydrolyzed soy fraction.

FIG. 3 contains the results of a calcium imaging assay that demonstrated that cell lines stably expressing hT2R1 specifically responded to methylthiourea.

FIG. 4 contains the results of a calcium imaging assay that demonstrated that cell lines stably expressing hT2R67 specifically responded to andrographolide.

DETAILED DESCRIPTION OF THE INVENTION

Prior to specifically describing the invention, the following definitions are provided.

The term "T2R" family includes polymorphic variants, alleles, mutants, and homologs that: (1) have about 30-40% amino acid sequence identity, more specifically about 40, 50, 60, 70, 75, 80, 85, 90, 95, 96, 97, 98, or 99% amino acid sequence identity to the T2R5 disclosed infra, and in the Zuker (Id) (2001) and Adler (Id.) (2001) applications incorporated, by reference herein over a window of about 25 amino acids, optimally 50-100 amino acids; (2) specifically bind to antibodies raised against an immunogen comprising an amino acid sequence selected from the group consisting of the T2R sequences disclosed infra, and conservatively modified variants thereof; (3) specifically hybridize (with a size of at least about 100, optionally at least about 500-1000 nucleotides) under stringent hybridization conditions to a sequence selected from the group consisting of the T2R DNA sequences disclosed infra, and conservatively modified variants thereof; (4) comprise a sequence at least about 40% identical to an amino acid sequence selected from the group consisting of the T2R amino acid sequences disclosed infra or (5) are amplified by primers that specifically hybridize under stringent hybridization conditions to the described T2R sequences.

In particular, these "T2Rs" include taste receptor GPCRs referred to herein as hT2R1, hT2R3, hT2R4, hT2R5, hT2R7, hT2R8, hT2R9A, hT2R9V, hT2R10, hT2R13, hT2R14, hT2R16, hT2R44, hT2R50, hT2R54, hT2R55, hT2R61, hT2R64, hT2R65, hT2R67, hT2R71, hT2R75, and hT2R76 having the nucleic acid sequences and amino acid sequences provided in this application, and variants, alleles, mutants, orthologs and chimeras thereof which specifically bind to bitter ligands which are identified herein and other structurally related compounds and bitter compounds.

While T2R genes exhibit substantial sequence divergence at both the protein and DNA level, all T2Rs isolated to date have been found to contain certain consensus sequences in particular regions that are identical or which possess or at least 70-75% sequence identity to the T2R consensus sequence identified previously in the Adler et al (WO 01/77676 A1 (2001) and Zuker et al. WO 01/18050 A2, both incorporated by reference in their entirety herein.

Topologically, certain chemosensory GPCRs have an "N-terminal domain" "extracellular domains," a "transmembrane domain" comprising seven transmembrane regions, and corresponding cytoplasmic and extracellular loops, "cytoplasmic regions," and a "C-terminal region" (see, e.g., Hoon et al, Cell, 96:541-51 (1999); Buck & Axel, Cell, 65:175-87 (1991)). These regions can be structurally identified using methods known to those of skill in the art, such as sequence analysis programs that identify hydrophobic and hydrophilic domains (see, e.g., Stryer, Biochemistry, (3rd ed. 1988); see also any of a number of Internet based sequence analysis programs, such as those found at dot.imgen.bcm.tmc.edu). These regions are useful for making chimeric proteins and for in vitro assays of the invention, e.g., ligand binding assays. For example chimeric T2Rs can be made by combining the extracellular region of one T2R and the transmembrane region of another T2R of the same or different species.

"Extracellular domains" therefore refers to the domains of T2R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful for in vitro ligand binding assays.

"T2R expressing cell" herein encompasses recombinant cells which express a human T2R sequence according to the invention as well as endogenous T2R expressing cells. Such cells are comprised in the lingual and gastrointestinal system and include cells in the oral cavity such as taste buds expressed on the tongue as well as cells in the gastrointestinal system and associated organs such as brush cells in the gastrointestinal tract, enteroendocrine cells such as STC-1 cells. These cells may also express a G protein such as gustducin, transducin, Galpha15 or Galpha16. Cells which express specific T2Rs can be identified and isolated by known methods such as by FACS cell separation of magnetic bead cell isolation procedures.

"Transmembrane domain," which comprises the seven transmembrane "regions," refers to the domain of T2R polypeptides that lies within the plasma membrane, and may also include the corresponding cytoplasmic (intracellular) and extracellular loops, also referred to as transmembrane "regions." The seven transmembrane regions and extracellular and cytoplasmic loops can be identified using standard methods, as described in Kyte & Doolittle, J. Mol. Biol., 157:105-32 (1982)), or in Stryer, supra.

"Cytoplasmic domains" refers to the domains of T2R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" means a polypeptide belonging to a superfamily of transmembrane proteins that have seven regions that span the plasma membrane seven times (thus, the seven regions are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "ligand-binding region" refers to sequences derived from a chemosensory or taste receptor that substantially incorporates transmembrane domains II to VII (TM II to VII). The region may be capable of binding a ligand, and more particularly, a taste eliciting compound.

The term "plasma membrane translocation domain" or simply "translocation domain" means a polypeptide domain which when incorporated into the amino terminus of a polypeptide coding sequence, can with great efficiency "chaperone" or "translocate" the hybrid ("fusion") protein to the cell plasma membrane. For example a particular "translocation domain" initially derived from the amino terminus of the human rhodopsin receptor polypeptide, a 7-transmembrane receptor can be used. Another translocation domain has been derived from the bovine rhodopsin sequence and is also useful for facilitating translocation. Rhodopsin derived sequences are particularly efficient in translocating 7-transmembrane fusion proteins to the plasma membrane.

"Functional equivalency" means the domain's ability and efficiency in translocating newly translated proteins to the plasma membrane as efficiently as an exemplary translocation domain such as one derived from rhodopsin under similar conditions; relative efficiencies can be measured (in quantitative terms) and compared, as described herein. Domains falling within the scope of the invention can be determined by routine screening for their efficiency in translocating newly synthesized polypeptides to the plasma membrane in a cell (mammalian, Xenopus, and the like) with the same efficiency as the twenty amino acid long translocation domain SEQ ID NO:1.

The phrase "functional effects" in the context of assays for testing compounds that modulate T2R family member mediated taste transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of a T2R family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte T2R gene expression; tissue culture cell T2R expression; transcriptional activation of T2R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of T2R proteins receptors are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate taste transduction, e.g., agonists. Modulators include compounds that, e.g., alter the interaction of a receptor with extracellular proteins that bind activators or inhibitor (e.g., ebnerin and other members of the hydrophobic carrier family); G Proteins; kinases (e.g., homologs of rhodopsin kinase and beta adrenergic receptor kinases that are involved in deactivation and desensitization of a receptor); and arresting, which also deactivate and desensitize receptors. Modulators include genetically modified versions of T2R family members, e.g., with altered activity, as well as naturally occurring and synthetic ligands, antagonists, agonists, small chemical molecules and the like.

Such assays for inhibitors and activators include, e.g., expressing T2R family members in cells or cell membranes, applying putative modulator compounds in the presence or absence of compounds that modulate, e.g., bitter compounds, and then determining the functional effects on taste transduction, as described above. Samples or assays comprising T2R family members that are treated with a potential activator, inhibitor, or modulator are compared to control samples without the inhibitor, activator, or modulator to examine the extent of modulation. Control samples (untreated with modulators) are assigned a relative T2R activity value of 100%. Inhibition of a T2R is achieved when the T2R activity value relative to the control is about 80%, optionally 50% or 25-0%. Activation of a T2R is achieved when the T2R activity value relative to the control is 110%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state. Preferably, "purified," "substantially purified," and "isolated" means that the composition comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated", when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein. The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant or naturally expressed nucleic acid, as described in detail, below. For example, the invention provides methods and reagents (e.g., specific oligonucleotide primer pairs) for amplifying (e.g., by polymerase chain reaction, PCR) naturally expressed (e.g., genomic or mRNA) or recombinant (e.g., cDNA) nucleic acids of the invention (e.g., taste eliciting compound-binding sequences of the invention) in vivo or in vitro.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes" which contain only the minimum elements needed for transcription of the recombinant nucleic acid.

The term "library" means a preparation that is a mixture of different nucleic acid or poly-peptide molecules, such as the library of recombinant generated sensory, particularly taste receptor ligand-binding regions generated by amplification of nucleic acid with degenerate primer pairs, or an isolated collection of vectors that incorporate the amplified ligand-binding regions, or a mixture of cells each randomly transfected with at least one vector encoding an taste receptor.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues (Batzer et al., Nucleic Acid Res., 19:5081 (1991); Ohtsuka et al., J. Biol. Chem., 260:2605-08 (1985); Rossolini et al., Mol. Cell. Probes, 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The "translocation domain," "ligand-binding region", and chimeric receptors compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine. Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser;

gin/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W. H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., translocation domains, ligand-binding regions, or chimeric receptors of the invention. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(.=O)—$CH_2$ for —C(.=O)—NH—), aminomethylene ($CH_2NH$), ethylene, olefin (CH.dbd.CH), ether ($CH_2O$), thioether ($CH_2$—S), tetrazole ($CN_4$), thiazole, retroamide, thioamide, or ester (see, e.g., Spatola, Chemistry and Biochemistry of Amino Acids, Peptides and Proteins, Vol. 7, 267-357, Marcell Dekker, Peptide Backbone Modifications, NY (1983)). A polypeptide can also be characterized as a mimetic by containing all or some non-natural residues in place of naturally occurring amino acid residues; non-natural residues are well described in the scientific and patent literature.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence. The promoter may be used in polycistronic and monocistronic vector systems to regulate the expression of one of more structural genes as desired.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant means" also encompass the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such hybridizations and wash steps can be carried out for, e.g., 1, 2, 5, 10, 15, 30, 60; or more minutes.

Nucleic acids that do not hybridize to each other under stringent conditions are still substantially related if the polypeptides which they encode are substantially related. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such hybridizations and wash steps can be carried out for, e.g., 1, 2, 5, 10, 15, 30, 60, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-T2R" antibody is an antibody or antibody fragment that specifically binds a polypeptide encoded by a T2R gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or, "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein.

For example, polyclonal antibodies raised to a T2R family member from specific species such as rat, mouse, or human can be selected to obtain only those polyclonal antibodies that are specifically immunoreactive with the T2R polypeptide or an immunogenic portion thereof and not with other proteins, except for orthologs or polymorphic variants and alleles of the T2R polypeptide. This selection may be achieved by subtracting out antibodies that cross-react with T2R molecules from other species or other T2R molecules. Antibodies can also be selected that recognize only T2R GPCR family members but not GPCRs from other families. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual, (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to" a protein, as defined above.

The term "expression vector" refers to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes" which contain only the minimum elements needed for transcription of the recombinant nucleic acid.

By "host cell" is meant a cell that contains an expression vector and supports the replication or expression of the expression vector. Host cells may be prokaryotic cells such as E. coli, or eukaryotic cells such as yeast, insect, amphibian, or mammalian cells such as CHO, HeLa, HEK-293, and the like, e.g., cultured cells, explants, and cells in vivo.

Based on the foregoing, the present invention provides assays for identifying compounds that modulate, preferably block, the specific activation of the previously identified human bitter taste receptor by bitter compounds present in hydrolyzed soy proteins and other ingestibles, e.g., the bitter compounds identified in FIGS. 3 and 4 and structurally related and other bitter compounds. Particularly, the invention provides cell-based assays for identifying compounds that modulate (e.g., block) the activation of hT2R1 or hT2R67 by hydrolyzed soy protein, a bitter compound contained therein or specifically one of the bitter ligands shown to activate these specific taste receptors identified in FIGS. 3 and 4 or another structurally related or another bitter compound. These compounds will modulate bitter taste of hydrolyzed soy protein containing ingestibles or containing bitter ligands present therein such as the bitter peptides mentioned supra that would otherwise be elicited by these taste receptors upon ingestion of hydrolozed soy containing products by human subjects. As mentioned previously this includes by way of example various types of comestibles for human or animal consumption, pharmaceuticals, nutriceuticals, and oral hygiene compositions. That these identified compounds inhibit bitter taste may be confirmed in taste tests.

That the above taste receptors specifically respond to bitter ligands present in hydrolyzed soy protein as shown in FIGS. 2-4 was determined essentially using the HEK293 expression system and calcium imaging methods reported in other publications as well as patent applications filed by the present Assignee, e.g., U.S. Ser. Nos. 10/191,058, 09/825,882, 11/555,617 and 11/766,974 all of which are both incorporated by reference in their entireties herein. More particularly, the present inventors transfected HEK293 cells with a particular hT2R tagged with a rhodopsin 35 amino acid tag (SEQ ID NO:1) together with a chimeric G protein (G16gust44) which comprises the $G_{\alpha 16}$ G protein sequence modified by the replacement of carboxy-44 amino acid residues with those of gustducin, and recorded responses of these cells to specific bitter ligands by calcium imaging methods.

Specifically, the inventors used a mammalian cell-based assay to monitor hT2R activities. For calcium imaging assays, cells were seeded into 48-well tissue culture plates. 24 hours later the cells were transiently transfected with an expression plasmid (pEAK10) containing an hT2R nucleic acid sequence, and a plasmid (pEAK10) containing a chimeric G protein (G16gust44). Another 24 hours later the cells were incubated with a fluorescent dye specific for calcium (Fluo-4; Molecular Probes). The loaded cells are exposed to different bitter molecules, and the activation of an hT2R leads to activation of G16gust44, which in turn leads to calcium mobilization inside within the cells. This increase in calcium concentration changes the fluorescence properties of the calcium dye inside the cells. These changes are monitored using fluorescence microscopy.

The inventors also used the automated fluorimetric aiming system FLIPR using a slightly different protocol. A HEK293 cell line stably expressing G16gust44 was transfected with a hT2R expression plasmid, 24 hours later, the cells are loaded and analyzed on FLIPR.

After a ligand is identified for a particular hT2R, a HEK293 cell line stably expressing both the hT2R and G16gust44 are generated facilitating future screening assays to identify other ligands that activate the particular hT2R or which modulate (block or enhance) the activation of this hT2R by another bitter ligand such as a compound identified in FIG. 2. This avoids the need for transient transfection.

As shown in the Figures such experiments demonstrated that both hT2R1 and hT2R67 specifically respond to hydrolyzed soy protein fractions and bitter compounds contained therein whereas other tested hT2Rs did not under the same assay conditions.

These results indicate that cells which functionally express any one of the identified hT2R taste receptors may be used in assays to identify ligands present in hydrolyzed soy protein and other related ingestibles that modulate the bitter taste of hydrolyzed soy that is otherwise associated with at least one of said particular hT2Rs.

Preferably, these assays will utilize a test cell that expresses a DNA encoding an hT2R having one of the amino acid sequences identified infra. However, it is anticipated that fragments, orthologs, variants or chimeras of these receptor polypeptides which retain the functional properties of these bitter taste receptors, i.e., respond to some bitter compounds, will also be useful in these assays. Examples of such variants include splice variants, single nucleotide polymorphisms, allelic variants, and mutations produced by recombinant or chemical means, or naturally occurring. Means for isolation and expression of T2Rs, which are used in the assays of the present invention and assays which are contemplated for use in the present invention to identify compounds that inhibit activation of these receptors, are set forth below.

Isolation and Expression of T2Rs

Isolation and expression of the T2Rs, or fragments or variants thereof, of the invention can be effected by well-established cloning procedures using probes or primers constructed based on the T2R nucleic acids sequences disclosed in the application. Related T2R sequences may also be identified from human or other species genomic databases using the sequences disclosed herein and known computer-based search technologies, e.g., BLAST sequence searching. In a particular embodiment, the pseudogenes disclosed herein can be used to identify functional alleles or related genes.

Expression vectors can then be used to infect or transfect host cells for the functional expression of these sequences. These genes and vectors can be made and expressed in vitro or in vivo. One of skill will recognize that desired phenotypes for altering and controlling nucleic acid expression can be obtained by modulating the expression or activity of the genes and nucleic acids (e.g., promoters, enhancers and the like) within the vectors of the invention. Any of the known methods described for increasing or decreasing expression or activity can be used. The invention can be practiced in conjunction with any method or protocol known in the art, which are well described in the scientific and patent literature.

Alternatively, these nucleic acids can be synthesized in vitro by well-known chemical synthesis techniques, as described in, e.g., Carruthers, Cold Spring Harbor Symp. Quant. Biol. 47:411-18 (1982); Adams, Am. Chem. Soc., 105:661 (1983); Belousov, Nucleic Acids Res. 25:3440-3444 (1997); Frenkel, Free Radic. Biol. Med. 19:373-380 (1995); Blommers, Biochemistry 33:7886-7896 (1994); Narang, Meth. Enzymol. 68:90 (1979); Brown, Meth. Enzymol. 68:109 (1979); Beaucage, Tetra. Lett. 22:1859 (1981); U.S. Pat. No. 4,458,066. Double-stranded DNA fragments may then be obtained either by synthesizing the complementary strand and annealing the strands together under appropriate conditions, or by adding the complementary strand using DNA polymerase with an appropriate primer sequence.

Techniques for the manipulation of nucleic acids, such as, for example, for generating mutations in sequences, subcloning, labeling probes, sequencing, hybridization and the like are well described in the scientific and patent literature. See, e.g., Sambrook, ed., Molecular Cloning: A Laboratory Manual (2nd ed.), Vols. 1-3, Cold Spring Harbor Laboratory (1989); Ausubel, ed., Current Protocols in Molecular Biology, John Wiley & Sons, Inc., New York (1997); Tijssen, ed., Laboratory Techniques in Biochemistry and Molecular Biology Hybridization With Nucleic Acid Probes, Part I, Theory and Nucleic Acid Preparation, Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g., fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Oligonucleotide primers may be used to amplify nucleic acids encoding a T2R ligand-binding region. The nucleic acids described herein can also be cloned or measured quantitatively using amplification techniques. Amplification methods are also well known in the art, and include, e.g., polymerase chain reaction (PCR) (Innis ed., PCR Protocols, a Guide to Methods and Applications, Academic Press, N.Y. (1990); Innis ed., PCR Strategies, Academic Press, Inc., N.Y. (1995)); ligase chain reaction (LCR) (Wu, Genomics, 4:560 (1989); Landegren, Science, 241:1077 (1988); Barringer, Gene, 89:117 (1990)); transcription amplification (Kwoh, PNAS, 86:1173 (1989)); self-sustained sequence replication (Guatelli, PNAS, 87:1874 (1990)); Q Beta replicase amplification (Smith, J. Clin. Microbiol., 35:1477-91 (1997)); automated Q-beta replicase amplification assay (Burg, Mol. Cell. Probes, 10:257-71 (1996)); and other RNA polymerase mediated techniques (e.g., NASBA, Cangene, Mississauga, Ontario). See also, Berger, Methods Enzymol., 152:307-16 (1987); Sambrook; Ausubel; U.S. Pat. Nos. 4,683,195 and 4,683,202; Sooknanan, Biotechnology, 13:563-64 (1995).

Once amplified, the nucleic acids, either individually or as libraries, may be cloned according to methods known in the art, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" the PCR primer pair. For example, Pst I and Bsp E1 sites were designed into the exemplary primer pairs of the invention. These particular restriction sites have a sequence that, when ligated, are "in-frame" with respect to the 7-membrane receptor "donor" coding sequence into which they are spliced (the ligand-binding region coding sequence is internal to the 7-membrane polypeptide, thus, if it is desired that the construct be translated downstream of a restriction enzyme splice site, out of frame results should be avoided; this may not be necessary if the inserted ligand-binding region comprises substantially most of the transmembrane VII region). The primers can be designed to retain the original sequence of the "donor" 7-membrane receptor. Alternatively, the primers can encode amino acid residues that are conservative substitutions (e.g., hydrophobic for hydrophobic residue, see above discussion) or functionally benign substitutions (e.g., do not prevent plasma membrane insertion, cause cleavage by peptidase, cause abnormal folding of receptor, and the like).

The primer pairs may be designed to selectively amplify ligand-binding regions of T2R proteins. These binding regions may vary for different ligands; thus, what may be a minimal binding region for one ligand, may be too limiting for a second potential ligand. Thus, binding regions of different sizes comprising different domain structures may be amplified; for example, transmembrane (TM) domains II through VII, III through VII, III through VI or II through VI, or variations thereof (e.g., only a subsequence of a particular domain, mixing the order of the domains, and the like), of a 7-transmembrane T2R.

As domain structures and sequence of many 7-membrane T2R proteins are known, the skilled artisan can readily select domain-flanking and internal domain sequences as model sequences to design degenerate amplification primer pairs. For example, a nucleic acid sequence encoding domain regions II through VII can be generated by PCR amplification using a primer pair. To amplify a nucleic acid comprising transmembrane domain I (TM I) sequence, a degenerate primer can be designed from a nucleic acid that encodes the amino acid sequence of the T2R family consensus sequence 1 described above. Such a degenerate primer can be used to generate a binding region incorporating TM I through TM III, TM I through TM IV, TM I through TM V, TM I through TM VI or TM I through TM VII). Other degenerate primers can be designed based on the other T2R family consensus sequences provided herein. Such a degenerate primer can be used to generate a binding region incorporating TM III through TM IV, TM III through TM V, TM III through TM VI or TM III through TM VII.

Paradigms to design degenerate primer pairs are well known in the art. For example, a COnsensus-DEgenerate Hybrid Oligonucleotide Primer (CODEHOP) strategy computer program is accessible as http://blocks.fhcrc.org/codehop.html, and is directly linked from the BlockMaker multiple sequence alignment site for hybrid primer prediction beginning with a set of related protein sequences, as known taste receptor ligand-binding regions (see, e.g., Rose, Nucleic Acids Res., 26:1628-35 (1998); Singh, Biotechniques, 24:318-19 (1998)).

Means to synthesize oligonucleotide primer pairs are well known in the art. "Natural" base pairs or synthetic base pairs can be used. For example, use of artificial nucleobases offers a versatile approach to manipulate primer sequence and generate a more complex mixture of amplification products. Various families of artificial nucleobases are capable of assuming multiple hydrogen bonding orientations through internal bond rotations to provide a means for degenerate molecular recognition. Incorporation of these analogs into a single position of a PCR primer allows for generation of a complex library of amplification products. See, e.g., Hoops, Nucleic Acids Res., 25:4866-71 (1997). Nonpolar molecules can also be used to mimic the shape of natural DNA bases. A non-hydrogen-bonding shape mimic for adenine can replicate efficiently and selectively against a nonpolar shape mimic for thymine (see, e.g., Morales, Nat. Struct. Biol., 5:950-54 (1998)). For example, two degenerate bases can be the pyrimidine base 6H, 8H-3,4-dihydropyrimido[4,5-c][1,2]oxazin-7-one or the purine base N6-methoxy-2,6-diaminopurine (see, e.g., Hill, PNAS, 95:4258-63 (1998)). Exemplary degenerate primers of the invention incorporate the nucleobase analog 5'-Dimethoxytrityl-N-benzoyl-2'-deoxy-Cytidine,3'-[(2-cyanoethyl)-(N,N-diisopropyl)]-phosphoramidite (the term "P" in the sequences, see above). This pyrimidine analog hydrogen bonds with purines, including A and G residues.

Polymorphic variants, alleles, and interspecies homologs that are substantially identical to a taste receptor disclosed herein can be isolated using the nucleic acid probes described above. Alternatively, expression libraries can be used to clone T2R polypeptides and polymorphic variants, alleles, and interspecies homologs thereof, by detecting expressed homologs immunologically with antisera or purified antibodies made against a T2R polypeptide, which also recognize and selectively bind to the T2R homolog.

Nucleic acids that encode ligand-binding regions of taste receptors may be generated by amplification (e.g., PCR) of appropriate nucleic acid sequences using appropriate (perfect or degenerate) primer pairs. The amplified nucleic acid can be genomic DNA from any cell or tissue or mRNA or cDNA derived from taste receptor-expressing cells.

In one embodiment, hybrid protein-coding sequences comprising nucleic acids encoding T2Rs fused to a translocation sequences may be constructed. Also provided are hybrid T2Rs comprising the translocation motifs and taste eliciting compound-binding regions of other families of chemosensory receptors, particularly taste receptors. These nucleic acid sequences can be operably linked to transcriptional or translational control elements, e.g., transcription and translation initiation sequences, promoters and enhancers, transcription and translation terminators, polyadenylation sequences, and other sequences useful for transcribing DNA into RNA. In construction of recombinant expression cassettes, vectors, and transgenics, a promoter fragment can be employed to direct expression of the desired nucleic acid in all desired cells or tissues.

In another embodiment, fusion proteins may include C-terminal or N-terminal translocation sequences. Further, fusion proteins can comprise additional elements, e.g., for protein detection, purification, or other applications. Detection and purification facilitating domains include, e.g., metal chelating peptides such as polyhistidine tracts, histidine-tryptophan modules, or other domains that allow purification on immobilized metals; maltose binding protein; protein A domains that allow purification on immobilized immunoglobulin; or the domain utilized in the FLAGS extension/affinity purification system (Immunex Corp, Seattle Wash.).

The inclusion of a cleavable linker sequences such as Factor Xa (see, e.g., Ottavi, Biochimie, 80:289-93 (1998)), subtilisin protease recognition motif (see, e.g., Polyak, Protein Eng., 10:615-19 (1997)); enterokinase (Invitrogen, San Diego, Calif.), and the like, between the translocation domain (for efficient plasma membrane expression) and the rest of the newly translated polypeptide may be useful to facilitate purification. For example, one construct can include a polypeptide encoding a nucleic acid sequence linked to six histidine residues followed by a thioredoxin, an enterokinase cleavage site (see, e.g., Williams, Biochemistry, 34:1787-97 (1995)), and an C-terminal translocation domain. The histidine residues facilitate detection and purification while the enterokinase cleavage site provides a means for purifying the desired protein(s) from the remainder of the fusion protein. Technology pertaining to vectors encoding fusion proteins and application of fusion proteins are well described in the scientific and patent literature (see, e.g., Kroll, DNA Cell. Biol,. 12:441-53 (1993)).

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Roberts, Nature, 328:731 (1987); Berger supra; Schneider, Protein Exper. Purif., 6435:10 (1995); Sambrook; Tijssen; Ausubel. Product information from manufacturers of biological reagents and experimental equipment also provide information regarding known biological methods. The vectors can be isolated from natural sources, obtained from such sources as ATCC or GenBank libraries, or prepared by synthetic or recombinant methods.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences (see, e.g., Blondelet-Rouault, Gene, 190:315-17 (1997); Aubrecht, J. Pharmacol. Exp. Ther., 281:992-97 (1997)). Because selectable marker genes conferring resistance to substrates like neomycin or hygromycin can only be utilized in tissue culture, chemoresistance genes are also used as selectable markers in vitro and in vivo.

A chimeric nucleic acid sequence may encode a T2R ligand-binding region within any 7-transmembrane polypeptide. Because 7-transmembrane receptor polypeptides have similar primary sequences and secondary and tertiary structures, structural domains (e.g., extracellular domain, TM domains, cytoplasmic domain, etc.) can be readily identified by sequence analysis. For example, homology modeling, Fourier analysis and helical periodicity detection can identify and characterize the seven domains with a 7-transmembrane receptor sequence. Fast Fourier Transform (FFT) algorithms can be used to assess the dominant periods that characterize profiles of the hydrophobicity and variability of analyzed sequences. Periodicity detection enhancement and alpha helical periodicity index can be done as by, e.g., Donnelly, Protein Sci., 2:55-70 (1993). Other alignment and modeling algorithms are well known in the art (see, e.g., Peitsch, Receptors Channels, 4:161-64 (1996); Kyte & Doolittle, J. Md. Biol., 157:105-32 (1982); and Cronet, Protein Eng., 6:59-64 (1993).

The present invention also includes not only the nucleic acid molecules and polypeptides having the specified nucleic and amino acid sequences, but also fragments thereof, particularly fragments of, e.g., 40, 60, 80, 100, 150, 200, or 250 nucleotides, or more, as well as polypeptide fragments of, e.g., 10, 20, 30, 50, 70, 100, or 150 amino acids, or more. Optionally, the nucleic acid fragments can encode an antigenic polypeptide that is capable of binding to an antibody raised against a T2R family member. Further, a protein fragment of the invention can optionally be an antigenic fragment that is capable of binding to an antibody raised against a T2R family member.

Also contemplated are chimeric proteins, comprising at least 10, 20, 30, 50, 70, 100, or 150 amino acids, or more, of one of at least one of the T2R polypeptides described herein, coupled to additional amino acids representing all or part of another GPCR, preferably a member of the 7 transmembrane superfamily. These chimeras can be made from the instant receptors and another GPCR, or they can be made by combining two or more of the present receptors. In one embodiment, one portion of the chimera corresponds to, or is derived from the transmembrane domain of a T2R polypeptide of the invention. In another embodiment, one portion of the chimera corresponds to, or is derived from the one or more of the transmembrane regions of a T2R polypeptide described herein, and the remaining portion or portions can come from another GPCR. Chimeric receptors are well known in the art, and the techniques for creating them and the selection and boundaries of domains or fragments of G Protein-Coupled Receptors for incorporation therein are also well known. Thus, this knowledge of those skilled in the art can readily be used to create such chimeric receptors. The use of such chimeric receptors can provide, for example, a taste selectivity characteristic of one of the receptors specifically disclosed herein, coupled with the signal transduction characteristics of another receptor, such as a well known receptor used in prior art assay systems.

For example, a region such as a ligand-binding region, an extracellular domain, a transmembrane domain, a transmembrane domain, a cytoplasmic domain, an N-terminal domain, a C-terminal domain, or any combination thereof, can be covalently linked to a heterologous protein. For instance, a T2R transmembrane region can be linked to a heterologous GPCR transmembrane domain, or a heterologous GPCR extracellular domain can be linked to a T2R transmembrane region. Other heterologous proteins of choice can include, e.g., green fluorescent protein, .beta.-galactosidase polypeptides, glutamate receptor, and the rhodopsin polypeptides, e.g., N-terminal fragments of rhodopsin e.g., bovine rhodopsin.

It is also within the scope of the invention to use different host cells for expressing the T2Rs, fragments, or variants of the invention. To obtain high levels of expression of a cloned gene or nucleic acid, such as cDNAs encoding the T2Rs, fragments, or variants of the invention, one of skill typically subclones the nucleic acid sequence of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. Preferably, eukaryotic expression systems are used to express the subject hT2R receptor.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al.) It is only necessary that the particular genetic engineering procedure used be capable of successfully introducing at lest one nucleic acid molecule into the host cell capable of expressing the T2R, fragment, or variant of interest.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593, which is incorporated by reference in a manner consistent with this disclosure.

Assays for Detection of Compounds That Modulate the Activity of a hT2R According to the Invention Methods and compositions for determining whether a test compound specifically binds to a T2R polypeptide of the invention, both in vitro and in vivo are described below. Many aspects of cell physiology can be monitored to assess the effect of ligand-binding to a naturally occurring or chimeric T2Rs. These assays may be performed on intact cells expressing a T2R polypeptide, on permeabilized cells, or on membrane fractions produced by standard methods.

Taste receptors bind taste eliciting compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

The subject hT2R proteins or polypeptides of the assay will typically be selected from a polypeptide having a sequence contained in the sequence listing preceding the claims herein or fragments or conservatively modified variants thereof.

Alternatively, the T2R proteins or polypeptides of the assay can be derived from a eukaryotic host cell, and can include an amino acid sequence having a certain percentage amino acid sequence identity to these hT2R polypeptides or conservatively modified variants thereof. Generally, the amino acid sequence identity will be at least 30% preferably 30-40%, more specifically 50-60, 70%, 75%, 80%, 85%, 90%, 95%, 96%, 97%, 98%, or 99%. Optionally, the T2R proteins or polypeptides of the assays can comprise a region of a T2R polypeptide, such as an extracellular domain, transmembrane region, cytoplasmic domain, ligand-binding domain, and the like. Optionally, as exemplified herein the T2R polypeptide, or a portion thereof, can be covalently linked to a heterologous protein to create a chimeric protein used in the assays described herein.

Modulators of T2R activity may be tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

Detection of Modulators

Compositions and methods for determining whether a test compound specifically binds to a T2R receptor of the invention, both in vitro and in vivo, are described below. Many aspects of cell physiology can be monitored to assess the effect of ligand binding to a T2R polypeptide of the invention. These assays may be performed on intact cells expressing a chemosensory receptor, on permeabilized cells, or on membrane fractions produced by standard methods or in vitro using de novo synthesized proteins.

In vivo, taste receptors bind to taste modulatory compounds and initiate the transduction of chemical stimuli into electrical signals. An activated or inhibited G protein will in turn alter the properties of target enzymes, channels, and other effector proteins. Some examples are the activation of cGMP phosphodiesterase by transducin in the visual system, adenylate cyclase by the stimulatory G protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Alternatively, the T2R proteins or polypeptides of the assay can be derived from a eukaryotic host cell and can include an amino acid subsequence having amino acid sequence identity to the T2R polypeptides disclosed herein, or fragments or conservatively modified variants thereof. Generally, the amino acid sequence identity will be at least 35 to 50%, or optionally 75%, 85%, 90%, 95%, 96%, 97%, 98%, or 99%. Optionally, the T2R proteins or polypeptides of the assays can comprise a domain of a T2R protein, such as an extracellular domain, transmembrane region, transmembrane domain, cytoplasmic domain, ligand-binding domain, and the like. Further, as described above, the T2R protein or a domain thereof can be covalently linked to a heterologous protein to create a chimeric protein used in the assays described herein.

Modulators of T2R receptor activity are tested using T2R proteins or polypeptides as described above, either recombinant or naturally occurring. The T2R proteins or polypeptides can be isolated, expressed in a cell, expressed in a membrane derived from a cell, expressed in tissue or in an animal, either recombinant or naturally occurring. For example, tongue slices, dissociated cells from a tongue, transformed cells, or membranes can be used. Modulation can be tested using one of the in vitro or in vivo assays described herein.

1. In vitro Binding Assays

Taste transduction can also be examined in vitro with soluble or solid state reactions, using the T2R polypeptides of the invention. In a particular embodiment, T2R ligand-binding domains can be used in vitro in soluble or solid state reactions to assay for ligand binding.

It is possible that the ligand-binding domain may be formed by the N-terminal domain together with additional portions of the extracellular domain, such as the extracellular loops of the transmembrane domain.

In vitro binding assays have been used with other GPCRs, such as the metabotropic glutamate receptors (see, e.g., Han and Hampson, J. Biol. Chem. 274:10008-10013 (1999)). These assays might involve displacing a radioactively or fluorescently labeled ligand, measuring changes in intrinsic fluorescence or changes in proteolytic susceptibility, etc.

Ligand binding to a T2R polypeptide according to the invention can be tested in solution, in a bilayer membrane, optionally attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

In a preferred embodiment of the invention, a $[^{35,S}]$GTPγS binding assay is used. As described above, upon activation of a GPCR, the Gα subunit of the G protein complex is stimulated to exchange bound GDP for GTP. Ligand-mediated stimulation of G protein exchange activity can be measured in a biochemical assay measuring the binding of added radioactively labeled $[^{35,S}]$GTPγS to the G protein in the presence of a putative ligand. Typically, membranes containing the chemosensory receptor of interest are mixed with a G protein. Potential inhibitors and/or activators and $[^{35,S}]$GTPγS are added to the assay, and binding of $[^{35,S}]$GTPγS to the G protein is measured. Binding can be measured by liquid scintillation counting or by any other means known in the art, including scintillation proximity assays (SPA). In other assays formats, fluorescently labeled GTPγS can be utilized.

2. Fluorescence Polarization Assays

In another embodiment, Fluorescence Polarization ("FP") based assays may be used to detect and monitor ligand binding. Fluorescence polarization is a versatile laboratory technique for measuring equilibrium binding, nucleic acid hybridization, and enzymatic activity. Fluorescence polarization assays are homogeneous in that they do not require a separation step such as centrifugation, filtration, chromatography, precipitation, or electrophoresis. These assays are done in real time, directly in solution and do not require an immobilized phase. Polarization values can be measured repeatedly and after the addition of reagents since measuring the polarization is rapid and does not destroy the sample. Generally, this technique can be used to measure polarization values of fluorophores from low picomolar to micromolar levels. This section describes how fluorescence polarization can be used in a simple and quantitative way to measure the binding of ligands to the T2R polypeptides of the invention.

When a fluorescently labeled molecule is excited with plane polarized light, it emits light that has a degree of polarization that is inversely proportional to its molecular rotation. Large fluorescently labeled molecules remain relatively stationary during the excited state (4 nanoseconds in the case of fluorescein) and the polarization of the light remains relatively constant between excitation and emission. Small fluorescently labeled molecules rotate rapidly during the excited state and the polarization changes significantly between excitation and emission. Therefore, small molecules have low polarization values and large molecules have high polarization values. For example, a single-stranded fluorescein-labeled oligonucleotide has a relatively low polarization value but when it is hybridized to a complementary strand, it has a higher polarization value. When using FP to detect and monitor taste eliciting compound-binding which may activate or inhibit the chemosensory receptors of the invention, fluorescence-labeled taste eliciting compounds or auto-fluorescent taste eliciting compounds may be used.

Fluorescence polarization (P) is defined as:

$$P = \frac{[Int_{par} - Int_{perp}]}{[Int_{par} + Int_{perp}]}$$

Where . $Int_{par}$ is the intensity of the emission light parallel to the excitation light plane and $Int_{perp}$ is the intensity of the emission light perpendicular to the excitation light plane. P, being a ratio of light intensities, is a dimensionless number. For example, the Beacon™ and Beacon 2000™ System may be used in connection with these assays. Such systems typically express polarization in millipolarization units (1 Polarization Unit=1000 mP Units).

The relationship between molecular rotation and size is described by the Perrin equation and the reader is referred to Jolley, M. E. (1991) in Journal of Analytical Toxicology, pp. 236-240 incorporated by reference, which gives a thorough explanation of this equation. Summarily, the Perrin equation states that polarization is directly proportional to the rotational relaxation time, the time that it takes a molecule to rotate through an angle of approximately 68.5°. Rotational relaxation time is related to viscosity (eta.), absolute temperature (T), molecular volume (V), and the gas constant (R) by the following equation: 2(Rotational Relaxation Time)=3 V RT The rotational relaxation time is small (≃nanosecond) for small molecules (e.g. fluorescein) and large (≃100 nanoseconds) for large molecules (e.g. immunoglobulins). If viscosity and temperature are held constant, rotational relaxation time, and therefore polarization, is directly related to the molecular volume. Changes in molecular volume may be due to interactions with other molecules, dissociation, polymerization, degradation, hybridization, or conformational changes of the fluorescently labeled molecule. For example, fluorescence polarization has been used to measure enzymatic cleavage of large fluorescein labeled polymers by proteases, DNases, and RNases. It also has been used to measure equilibrium binding for protein/protein interactions, antibody/antigen binding, and protein/DNA binding.

B. A. Solid State and Soluble High Throughput Assays

In yet another embodiment, the invention provides soluble assays using a T2R polypeptide; or a cell or tissue expressing a T2R polypeptide. In another embodiment, the invention provides solid phase based in vitro assays in a high throughput format, where the T2R polypeptide, or cell or tissue expressing the T2R polypeptide is attached to a solid phase substrate or a taste stimulating compound and contacted with a T2R receptor, and binding detected using an appropriate tag or antibody raised against the T2R receptor.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 1000 to about 1500 different compounds. It is also possible to assay multiple compounds in each plate well. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc., 85:2149-2154 (1963) (describing solid phase synthesis of, e.g., peptides); Geysen et al., J. Immun. Meth., 102:259-274 (1987) (describing synthesis of solid phase components on pins); Frank & Doring, Tetrahedron, 44:60316040 (1988) (describing synthesis of various peptide sequences on cellulose disks); Fodor et al., Science, 251:767-777 (1991); Sheldon et al., Clinical Chemistry, 39(4):718-719 (1993); and Kozal et al., Nature Medicine, 2(7):753759 (1996) (all describing arrays of biopolymers fixed to solid substrates). Non-chemical approaches for fixing tag binders to substrates include other common methods, such as heat, cross-linking by UV radiation, and the like.

3. Cell-based Assays

In one preferred embodiment, a T2R protein is expressed in a eukaryotic cell either in unmodified forms or as chimeric, variant or truncated receptors with or preferably without a heterologous, chaperone sequence that facilitates its maturation and targeting through the secretory pathway. Such T2R polypeptides can be expressed in any eukaryotic cell, such as HEK-293 cells. Preferably, the cells comprise a functional G protein, e.g., $G_{\alpha15}$, or a chimeric $G_{\alpha16}$, gustducin or transducin or a chimeric G protein such as G16gust44 that is capable of coupling the chimeric receptor to an intracellular signaling pathway or to a signaling protein such as phospholipase C. Activation of T2R receptors in such cells can be detected using any standard method, such as by detecting changes in intracellular calcium by detecting FURA-2 dependent fluorescence in the cell. Such an assay is the basis of the experimental findings presented in this application.

Activated GPCR receptors often are substrates for kinases that phosphorylate the C-terminal tail of the receptor (and possibly other sites as well). Thus, activators will promote the transfer of $^{32}P$ from radiolabeled ATP to the receptor, which can be assayed with a scintillation counter. The phosphorylation of the C-terminal tail will promote the binding of arrestin-like proteins and will interfere with the binding of G proteins. For a general review of GPCR signal transduction and methods of assaying signal transduction, see, e.g., Methods in Enzymology, vols. 237 and 238 (1994) and volume 96 (1983); Bourne et al., Nature, 10:349:117-27 (1991); Bourne et al., Nature, 348:125-32 (1990); Pitcher et al., Annu. Rev. Biochem., 67:653-92 (1998).

T2R modulation may be assayed by comparing the response of T2R polypeptides treated with a putative T2R modulator to the response of an untreated control sample or a sample containing a known "positive" control. Such putative T2R modulators can include molecules that either inhibit or activate T2R polypeptide activity. In one embodiment, control samples treated with a compound that activates the T2R are assigned a relative T2R activity value of 100. Inhibition of a T2R polypeptide is achieved when the T2R activity value relative to the control sample is about 90%, optionally 50%, optionally 25-0%. Activation of a T2R polypeptide is achieved when the T2R activity value relative to the control is 110%, optionally 150%, 200-500%, or 1000-2000%.

Changes in ion flux may be assessed by determining changes in ionic polarization (i.e., electrical potential) of the cell or membrane expressing a T2R polypeptide. One means to determine changes in cellular polarization is by measuring changes in current (thereby measuring changes in polarization) with voltage-clamp and patch-clamp techniques (see, e.g., the "cell-attached" mode, the "inside-out" mode, and the "whole cell" mode, e.g., Ackerman et al., New Engl. J. Med., 336:1575-1595 (1997)). Whole cell currents are conveniently determined using the standard. Other known assays include: radiolabeled ion flux assays and fluorescence assays using voltage-sensitive dyes (see, e.g., Vestergarrd-Bogind et al., J. Membrane Biol., 88:67-75 (1988); Gonzales & Tsien, Chem. Biol., 4:269-277 (1997); Daniel et al., J. Pharmacol. Meth., 25:185-193 (1991); Holevinsky et al., J. Membrane Biology, 137:59-70 (1994)).

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as Ca2+, IP3, cGMP, or cAMP.

Preferred assays for GPCRs include cells that are loaded with ion or voltage sensitive dyes to report receptor activity. Assays for determining activity of such receptors can also use known agonists and antagonists for other G protein-coupled receptors as controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G protein-coupled receptors, promiscuous G proteins such as $G_{\alpha15}$ and $G_{\alpha16}$ can be used in the assay of choice (Wilkie et al., Proc. Nat'l Acad. Sci., 88:10049-10053 (1991)). Alternatively, other G proteins such as gustducin, transducin and chimeric G proteins such as $G_{\alpha16}$gust44 or Galpha16t25 may be used.

Receptor activation initiates subsequent intracellular events, e.g., increases in second messengers. Activation of some G protein-coupled receptors stimulates the formation of inositol triphosphate (IP3) through phospholipase C-mediated hydrolysis of phosphatidylinositol (Berridge & Irvine, Nature, 312:315-21 (1984)). IP3 in turn stimulates the release of intracellular calcium ion stores. Thus, a change in cytoplasmic calcium ion levels, or a change in second messenger levels such as IP3 can be used to assess G protein-coupled receptor function. Cells expressing such G protein-coupled receptors may exhibit increased cytoplasmic calcium levels as a result of contribution from both calcium release from intracellular stores and extracellular calcium entry via plasma membrane ion channels.

In a preferred embodiment, T2R polypeptide activity is measured by expressing T2R gene in a heterologous cell with a promiscuous G protein that links the receptor to a phospholipase C signal transduction pathway (see Offermanns & Simon, J. Biol. Chem., 270:15175-15180 (1995)). Preferably, the cell line is HEK-293 (which does not normally express T2R genes) and the promiscuous G protein is $G_{\alpha15}$ (Offermanns & Simon, supra) or a chimeric G protein such as Gα16gust44. Modulation of taste transduction is assayed by measuring changes in intracellular $Ca^{2+}$ levels, which change in response to modulation of the T2R signal transduction pathway via administration of a molecule that associates with the T2R polypeptide. Changes in $Ca^{2+}$ levels are optionally measured using fluorescent $Ca^{2+}$ indicator dyes and fluorimetric imaging.

In another embodiment, phosphatidyl inositol (PI) hydrolysis can be analyzed according to U.S. Pat. No. 5,436,128, herein incorporated by reference. Briefly, the assay involves labeling of cells with 3H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist, to cpm in the presence of buffer control. Likewise, fold inhibition is determined by calculating the ratio of cpm in the presence of antagonist, to cpm in the presence of buffer control (which may or may not contain an agonist).

Other receptor assays can involve determining the level of intracellular cyclic nucleotides, e.g., cAMP or cGMP. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. In one embodiment, the changes in intracellular cAMP or cGMP can be measured using immunoassays. The method described in Offermanns & Simon, J. Bio. Chem., 270:15175-15180 (1995), may be used to determine the level of cAMP. Also, the method described in Felley-Bosco et al., Am. J. Resp. Cell and Mol. Biol., 11:159-164 (1994), may be used to determine the level of cGMP. Further, an assay kit for measuring cAMP and/or cGMP is described in U.S. Pat. No. 4,115,538, herein incorporated by reference.

In another embodiment, transcription levels can be measured to assess the effects of a test compound on signal transduction. A host cell containing T2R polypeptide of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using a reporter gene may be used as described in U.S. Pat. No. 5,436,128, herein incorporated by reference. The reporter genes can be, e.g., chloramphenicol acetyltransferase, luciferase, beta-galactosidase, beta-lactamase and alkaline phosphatase. Furthermore, the protein of interest can be used as an indirect reporter via attachment to a second reporter such as green fluorescent protein (see, e.g., Mistili & Spector, Nature Biotechnology, 15:961-964 (1997)).

The amount of transcription is then compared to the amount of transcription in either the same cell in the absence of the test compound, or it may be compared with the amount of transcription in a substantially identical cell that lacks the T2R polypeptide(s) of interest. A substantially identical cell may be derived from the same cells from which the recombinant cell was prepared but which had not been modified by introduction of heterologous DNA. Any difference in the amount of transcription indicates that the test compound has in some manner altered the activity of the T2R polypeptide of interest.

4. Transgenic Non-human Animals Expressing Chemosensory Receptors

Non-human animals expressing one or more taste receptor sequences of the invention can also be used for receptor assays. Such expression can be used to determine whether a test compound specifically binds to a mammalian taste transmembrane receptor complex in vivo by contacting a non-human animal stably or transiently transfected with nucleic acids encoding chemosensory receptors or ligand-binding regions thereof with a test compound and determining whether the animal reacts to the test compound by specifically binding to the receptor polypeptide complex.

Animals transfected or infected with the vectors of the invention are particularly useful for assays to identify and characterize taste stimuli that can bind to a specific or sets of receptors. Such vector-infected animals expressing human taste receptor sequences can be used for in vivo screening of taste stimuli and their effect on, e.g., cell physiology (e.g., on taste neurons), on the CNS, or behavior.

Means to infect/express the nucleic acids and vectors, either individually or as libraries, are well known in the art. A variety of individual cell, organ, or whole animal parameters can be measured by a variety of means. The T2R sequences of the invention can be for example expressed in animal taste tissues by delivery with an infecting agent, e.g., adenovirus expression vector.

The endogenous taste receptor genes can remain functional and wild-type (native) activity can still be present. In other situations, where it is desirable that all taste receptor activity is by the introduced exogenous hybrid receptor, use of a knockout line is preferred. Methods for the construction of non-human transgenic animals, particularly transgenic mice, and the selection and preparation of recombinant constructs for generating transformed cells are well known in the art.

Construction of a "knockout" cell and animal is based on the premise that the level of expression of a particular gene in a mammalian cell can be decreased or completely abrogated by introducing into the genome a new DNA sequence that serves to interrupt some portion of the DNA sequence of the gene to be suppressed. Also, "gene trap insertion" can be used to disrupt a host gene, and mouse embryonic stem (ES) cells can be used to produce knockout transgenic animals (see, e.g., Holzschu, Transgenic Res 6:97-106 (1997)). The insertion of the exogenous is typically by homologous recombination between complementary nucleic acid sequences. The exogenous sequence is some portion of the target gene to be modified, such as exonic, intronic or transcriptional regulatory sequences, or any genomic sequence which is able to affect the level of the target gene's expression; or a combination thereof. Gene targeting via homologous recombination in pluripotential embryonic stem cells allows one to modify precisely the genomic sequence of interest. Any technique can be used to create, screen for, propagate, a knockout animal, e.g., see Bijvoet, Hum. Mol. Genet. 7:53-62 (1998); Moreadith, J. Mol. Med. 75:208-216 (1997); Tojo, Cytotechnology 19:161-165 (1995); Mudgett, Methods Mol. Biol. 48:167-184 (1995); Longo, Transgenic Res. 6:321-328 (1997); U.S. Pat. Nos. 5,616,491; 5,464,764; 5,631,153; 5,487,992; 5,627,059; 5,272,071; WO 91/09955; WO 93/09222; WO 96/29411; WO 95/31560; WO 91/12650.

The nucleic acids of the invention can also be used as reagents to produce "knockout" human cells and their progeny. Likewise, the nucleic acids of the invention can also be used as reagents to produce "knock-ins" in mice. The human or rat T2R gene sequences can replace the orthologs T2R in the mouse genome. In this way, a mouse expressing a human or rat T2R is produced. This mouse can then be used to analyze the function of human or rat T2Rs, and to identify ligands for such T2Rs.

Modulators

The compounds tested as modulators of a T2R family member can be any small chemical compound, or a biological entity, such as a protein, sugar, nucleic acid or lipid. Alternatively, modulators can be genetically altered versions of a T2R family member. Typically, test compounds may be small chemical molecules and peptides. Essentially any chemical compound can be used as a potential modulator or ligand in the assays of the invention, although most often compounds can be dissolved in aqueous or organic (especially DMSO-based) solutions are used. The assays may be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual consumer products.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res., 37:487-93 (1991) and Houghton et al., Nature, 354:84-88 (1991)). Other chemistries for generating chemical diversity libraries can also be used. Such chemistries include, but are not limited to: peptoids (e.g., WO 91/19735), encoded peptides (e.g., WO 93/20242), random bio-oligomers (e.g., WO 92/00091), benzodiazepines (e.g., U.S. Pat. No. 5,288,514), diversomers such as hydantoins, benzodiazepines and dipeptides (Hobbs et al., PNAS., 90:6909-13 (1993)), vinylogous polypeptides (Hagihara et al., J. Amer. Chem. Soc., 114:6568 (1992)), nonpeptidal peptidomimetics with glucose scaffolding (Hirschmann et al., J. Amer. Chem. Soc., 114:9217-18 (1992)), analogous organic syntheses of small compound libraries (Chen et al., J. Amer. Chem. Soc., 116:2661 (1994)), oligocarbamates (Cho et al., Science, 261:1303 (1993)), peptidyl phosphonates (Campbell et al., J. Org. Chem., 59:658 (1994)), nucleic acid libraries (Ausubel, Berger, and Sambrook, all supra), peptide nucleic acid libraries (U.S. Pat. No. 5,539,083), antibody libraries (Vaughn et al., Nature Biotechnology, 14(3):309-14 (1996) and PCT/US96/10287), carbohydrate libraries (Liang et al., Science, 274:1520-22 (1996) and U.S. Pat. No. 5,593, 853), small organic molecule libraries (benzodiazepines, Baum, C&EN, January 18, page 33 (1993); thiazolidinones and metathiazanones, U.S. Pat. No. 5,549,974; pynrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS (Advanced Chem Tech, Louisville Ky.), Symphony (Rainin, Woburn, Mass.), 433A (Applied Biosystems, Foster City, Calif.), 9050 Plus (Millipore, Bedford, Mass.)). In addition, numerous combinatorial libraries are themselves commercially available (see, e.g., ComGenex, Princeton, N.J.; Tripos, Inc., St. Louis, Mo.; 3D Pharmaceuticals, Exton, Pa.; Martek Biosciences; Columbia, Md.; etc.).

In one aspect of the invention, the T2R modulators can be used in any food product, confectionery, pharmaceutical composition, or ingredient thereof to thereby modulate the taste of the product, composition, or ingredient in a desired manner. For instance, T2R modulators that enhance bitter taste sensation can be added to provide a bitter taste to a product or composition, while T2R modulators which block bitter taste sensations can be added to block the bitter taste of a product or composition. Also, the invention provides means of identifying bitter compounds found in foods, beverages and medicinals and producing taste improved foods, beverages and medicinals lacking or having a reduced quantity thereof.

Use of Compounds Identified by the Invention

Compounds identified according to the invention may be added to hydrolyzed soy protein containing foods, beverages, cosmetics, nutriceuticals or medicinal compositions to modulate, preferably block bitter taste triggered by activation of hT2R1 or hT2R67 by hydrolyzed soy protein containing compositions or by at least one bitter compound present in hydrolyzed soy such as methylthiourea or andrographolide or structurally related compounds or other bitter compounds, e.g., compounds found in foods and beverages or medicinals or cosmetics that elicit a bitter taste perception.

As noted previously, preferably, the taste modulatory properties, preferably bitter taste blocking properties of compounds identified in the subject T2R cell-based assays will be confirmed in human or animal taste tests, preferably human taste tests. It is anticipated that these compounds when added to soy based products will reduce or even eliminate the bitter taste of hydrolyzed soy protein containing ingestibles thereby facilitating the production of soy products with desired functional properties such as promoting the reduction of serum cholesterol and improved taste.

Kits

T2R genes and their homologs are useful tools for identifying taste receptor cells, for forensics and paternity determinations, and for examining taste transduction. T2R family member-specific reagents that specifically hybridize to T2R nucleic acids, such as T2R probes and primers, and T2R specific reagents that specifically bind to a T2R protein, e.g., T2R antibodies are used to examine taste cell expression and taste transduction regulation.

Nucleic acid assays for the presence of DNA and RNA for a T2R family member in a sample include numerous techniques are known to those skilled in the art, such as southern analysis, northern analysis, dot blots, RNase protection, S1 analysis, amplification techniques such as PCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., Biotechniques, 4:230250 (1986); Haase et al., Methods in Virology, vol. VII, 189-226 (1984); and Names et al., eds., Nucleic Acid Hybridization: A Practical Approach (1987). In addition, a T2R protein can be detected with the various immunoassay techniques described above. The test sample is typically compared to both a positive control (e.g., a sample expressing a recombinant T2R protein) and a negative control.

The present invention also provides for kits for screening for modulators of T2R family members. Such kits can be prepared from readily available materials and reagents. For example, such kits can comprise any one or more of the following materials: T2R nucleic acids or proteins, reaction tubes, and instructions for testing T2R activity. Optionally, the kit contains a functional T2R polypeptide. A wide variety of kits and components can be prepared according to the present invention, depending upon the intended user of the kit and the particular needs of the user.

The present invention in particular provides for the use of the identified compounds and derivatives thereof in comestibles for human or animal consumption. This includes the use of the identified compounds in foods, beverages and medicines as flavor or taste modulators, i.e., to inhibit bitter taste, e.g., the bitter taste associated with specific beverages and foods or medicaments containing hydrolyzed soy proteins or bitter ligands present therein, especially bitter peptides produced during the hydrolysis of soy proteins.

As mentioned previously, these compounds may be used in any comestible containing soy proteins, especially hydrolyzed soy proteins or containing bitter ligands present therein. This includes comestibles for human and animal consumption. Examples thereof which are identified for illustrative purposes include by way of example, energy bars and gels; nutrition bars; meal replacements; dietary supplements; vitamins; non-dairy beverages/soymilk; meat alternatives (soy based); chips & snacks; tofu; dressings and condiments; frozen foods; ready meals; canned/preserved food; dried processed food; food supplements; cheese & cheese alternatives; soup, entrees & mixes; yogurt & kefir/soy yogurt & kefir; cookies & snack bars; cold cereals; baking mixes, supplies & flours (e.g. soy flour); confectionery; frozen fruits & vegetables (e.g. frozen green soybeans); bread & baked goods (frozen & non frozen); sauces, salsas & dips; pastas; puddings & desserts; herbal formulas; juices & functional drinks; seasonings; soynuts & mixes; packaged fresh produce; coffee, coffee substitutes & cocoa; hot cereals; beans, grains & rice; carbonated beverages other drinks; spreads, conserves, jams & nut butters/soynut butter; baked goods; dairy products and dairy alternatives; baby food/infant formula; chilled processed food; ice cream and frozen yogurt (including soy based); and clinical nutrition products.

In addition, the subject invention embraces any comestible, including animal feeds or pet foods containing such compounds including by way of example the use thereof in soy containing dog, bird, and cat food compositions, animal feeds for consumption by cattle, horses, goats or other farm animals, and animal feed compositions for use in feeding zoo animals.

Further, the invention embraces the use of these compounds in pharmaceuticals and compositions for use in oral hygiene such as tooth pastes, mouth washes, dentifrices, and the like.

Further, the invention embraces the production of food, beverages and medicinals which have been treated to remove compounds that specifically activate bitter taste receptors, e.g., foods and beverages that have been processed to remove or reduce the amount of bitter compounds comprised therein such as bitter peptides that activate hT2R1 or hT2R67 in the subject assays.

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLES

Materials and Methods

Hydrolyzed Soy Protein Preparation and Fractionation

Partial purification of hydrolyzed soy proteins was effected in order to enrich the bitter taste thereof. Specifically, 6.5 grams of hydrolyzed soy proteins were extracted with 130 milliliter of 65% ethanol for 1 hour at room temperature. The solution was centrifuged at 10,000 RPM for 30 minutes. The supernatant was lyophilized and re-suspended in 65 milliliter of 20% ethanol; reserved 20 milliliter as reference and 45 milliliter of the solution was applied to Reverse-phase column: Nova-Pak HR C18 (6 um, 60A, 19×300 mm) on an Agilent 1100 Prep HPLC-MSD. A gradient of 10% to 100% ethanol in 28 minutes at a flow rate of 25 milliliter per minute was used. Nine fractions designated F1 through F9 were collected as shown in FIG. 1 and the table 1 contained therein.

Each of the nine fractions was lyophilized and re-suspended in 65 milliliter of water, which is equivalent in concentration to 10% (W/V) of starting material. Taste test at 2 sets of concentrations were also performed. These taste tests determined that fractions F2 and F3 seem to contain most of the bitter taste from hydrolyzed soy proteins (Table 1).

Preparation of HEK293 Cell Lines and hT2R Functional Assays a. Cell Lines

As described in our previous patent applications, HEK293 cell transiently transfected with each of the 25 human T2Rs individually, with a chimeric G protein (G16t44) were generated which can be used in high throughput screening to find modulators of bitter taste mediated by different T2Rs.

b. Functional Assays

The activation of T2R receptors by different bitter ligands is measured in a cell-based assay detecting changes in intracellular calcium concentration. In brief, human embryonic kidney cells are seeded into 48-well tissue culture plates. 24 hours later these seeded HEK-293 cells are transiently transfected with an expression plasmid (pEAK10) containing a sequence encoding a chimeric G protein (G16gust44) (SEQ ID NO:2) and are also are transiently transfected with a pEAK10 expression plasmid containing a particular hT2R nucleic acid sequence either by $Ca^{2+}$ phosphate or lipid-based systems. Additionally, the hT2R sequences contained in the pEAK10 plasmid are each engineered to contain a Rho-35 tag or a SSTR-3 tag upstream of the hT2R sequence and therefore express an N-terminal tag of 35 amino acids of the rhodopsin protein (SEQ ID NO:1) or of 45 amino acids of SSTR-3 protein.

After another 24 hours the transiently transfected cells are incubated with a fluorescent dye specific for calcium (Fluo-4; Molecular Probes). These loaded cells are then exposed to different bitter molecules. Activation of the hT2R by a bitter ligand results in the activation of G16gust44, which leads to calcium mobilization within the cells. Thereupon this change in intracellular calcium causes the fluorescent dye to emit a detectable change in the fluorescence which is monitored using fluorescence microscopy. Particularly, this increase in calcium concentration changes the fluorescence properties of the calcium dye inside the cells and these changes are monitored using fluorescence microscopy and a specifically designed software (Imaging Workbench, Axon).

Also, the assay can be performed with the automated fluorimetric imaging system (FLIPR) using a slightly different protocol. In this protocol an HEK293 cell line stably expressing G16gust44 was transfected with an hT2R expression plasmid and 24 hours later the cells are dye loaded and analyzed on FLIPR.

Additionally, once a ligand is identified for a particular hT2R using this approach, a HEK-293 cell line is generated that stably expresses the particular hT2R and the chimeric G protein G16gust44.

Also, the assay can be performed with the automated fluorimetric imaging system (FLIPR) using a slightly different protocol. In this protocol an HEK293 cell line stably expressing G16gust44 was transfected with an hT2R expression plasmid and 24 hours later the cells are dye loaded and analyzed on FLIPR.

Applications of Compounds Identified Using hT2R1 and hT2R67 Based Assays Disclosed Herein The compounds identified using the assays disclosed herein have broad application in different comestibles for human and animal consumption. Soy, derived constituents given their intrinsic health benefits, as well as disclosed reducing effect of soy constituents on blood cholesterol levels are widely used in comestibles. Soybeans may be processed to yield different constituents and fractions including soy oil, soy milk, soy flour, soy lecithin, soy concentrates, and soy protein isolates. As described herein, the present invention especially uses the disclosed assays to identify compounds that alleviate the bitterness of compounds present in hydrolyzed soy protein containing compositions. While Applicants do not wish to be limited thereby, it is believed that the ligands present in hydrolyzed soy proteins which activate the hT2R1 and hT2R67 receptors include bitter peptides produced or retained during the hydrolysis process.

Based thereon, the compounds identified according to the subject assays which inhibit or block hT2R1 or hT2R67 activation by biter ligands, especially bitter peptides present in hydrolyzed soy protein compositions are useful as flavor additives in various comestibles especially those containing hydrolyzed soy proteins or bitter ligands present therein. s mentioned, this includes comestibles for human or animal consumption. More particularly this includes by way of illustration energy bars and gels; nutrition bars; meal replacements; dietary supplements; vitamins; non-dairy beverages/soymilk; meat alternatives (soy based); chips & snacks; tofu; dressings and condiments; frozen foods; ready meals; canned/preserved food; dried processed food; food supplements; cheese & cheese alternatives; soup, entrees & mixes; yogurt & kefir/soy yogurt & kefir; cookies & snack bars; cold cereals; baking mixes, supplies & flours (e.g. soy flour); confectionery; frozen fruits & vegetables (e.g. frozen green soybeans); bread & baked goods (frozen & non frozen); sauces, salsas & dips; pastas; puddings & desserts; herbal formulas; juices & functional drinks; seasonings; soynuts & mixes; packaged fresh produce; coffee, coffee substitutes & cocoa; hot cereals; beans, grains & rice; carbonated beverages other drinks; spreads, conserves, jams & nut butters/soynut butter; baked goods; dairy products and dairy alternatives; baby food/infant formula; chilled processed food; ice cream and frozen yogurt (including soy based); clinical nutrition products.

Also, this includes the use thereof in pet foods and foods for ingestion by agricultural or zoo animals. Also, this includes the use thereof in pharmaceuticals, nutriceuticals, and oral hygiene compositions.

Example 1

The bitter fractions derived from hydrolyzed soy protein shown in Table 1 were used in a HEK293 cell based T2R assay as described in our previous patent applications the contents of which are incorporated by reference herein in order to identify human T2R receptors that specifically respond to bitter fractions derived from hydrolyzed soy protein and in order to identify specific bitter compounds contained therein that specifically activate these bitter taste receptors. Cell lines stably expressing each of the 25 human T2Rs were tested. against fraction 3. These tests revealed that HEK293 cell lines stably transfected with hT2R1 and hT2R67 specifically responded to this bitter soy fraction.

FIG. 2 shows responses of each human T2R to soy protein fractions 3 (concentration is equivalent to 5% of starting material). Each trace represents one T2R responding to fraction 3, and each receptor were tested in quadruplets. The screening was done on FLIPR using HEK293 cells stably expressing G16g44 and transiently transfected with individual human T2Rs. The responses were reproduced multiple times, and hT2R1 and hT2R67 specific activities were observed each time.

FIG. 3 and FIG. 4 respectively show dose-dependent responses of hT2R1 and hT2R67 to methylthiourea and andrographolide.

(a)
SEQUENCES OF CHIMERIC G PROTEIN AND hT2R GENES AND POLYPEPTIDES
Protein Sequence of the Rhodopsin tag:

(SEQ ID NO: 1)
MNGTEGPNFYVPFSNKTGVVRSPFEAPQYYLAEPW

Protein Sequence of G16gust44:

(SEQ ID NO: 2)
MARSLTWRCCPWCLTEDEKAAARVDQEINRILLEQKKQDRGELKLLLLGP

GESGKSTFIKQMRIIHGAGYSEEERKGFRPLVYQNIFVSMRAMIEAMERL

QIPFSRPESKHHASLVMSQDPYKVTTFEKRYAAAMQWLWRDAGIRACYER

RREFHLLDSAVYYLSHLERITEEGYVPTAQDVLRSRMPTTGINEYCFSVQ

KTNLRIVDVGGQKSERKKWIHCFENVIALIYLASLSEYDQCLEENNQENR

MKESLALFGTILELPWFKSTSVILFLNKTDILEEKIPTSHLATYFPSFQG

PKQDAEAAKRFILDMYTRMYTGCVDGPEGSNLKKEDKEIYSHMTCATDTQ

NVKFVFDAVTDIIIKENLKDCGLF hT2R1 sequences
DNA- (SEQ ID NO: 3)
ATGCTAGAGTCTCACCTCATTATCTATTTTCTTCTTGCAGTGATACAATT

TCTTCTTGGGATTTTCACAAATGGCATCATTGTGGTGGTGAATGGCATTG

ACTTGATCAAGCACAGAAAAATGGCTCCGCTGGATCTCCTTCTTTCTTGT

CTGGCAGTTTCTAGAATTTTTCTGCAGTTGTTCATCTTCTACGTTAATGT

GATTGTTATCTTCTTCATAGAATTCATCATGTGTTCTGCGAATTGTGCAA

TTCTCTTATTTATcAATGAATTGGAACTTTGGCTTGCCACATGGCTCGGC

GTTTTCTATTGTGCCAAGGTTGCCAGCGTCCGTCACCCACTCTTCATCTG

GTTGAAGATGAGGATATCCAAGCTGGTCCCATGGATGATCCTGGGGTCTC

TGCTATATGTATCTATGATTTGTGTTTTCCATAGCAAATATGCAGGGTTT

ATGGTCCCATACTTCCTAAGGAAATTTTTCTCCCAAAATGCCACAATTCA

AAAAGAAGATACACTGGCTATACAGATTTTCTCTTTTGTTGCTGAGTTCT

CAGTGCCATTGCTTATCTTCCTTTTTGCTGTTTTGCTCTTGATTTTCTCT

```
CTGGGGAGGCACACCCGGCAAATGAGAAACACAGTGGCCGGCAGCAGGGT

TCCTGGCAGGGGTGCACCCATCAGCGCGTTGCTGTCTATCCTGTCCTTCC

TGATCCTCTACTTCTCCCACTGCATGATAAAAGTTTTTCTCTCTTCTCTA

AAGTTTCACATCAGAAGGTTCATCTTTCTGTTCTTCATCCTTGTGATTGG

TATATACCCTTCTGGACACTCTCTCATCTTAATTTTAGGAAATCCTAAAT

TGAAACAAAATGCAAAAAGTTCCTCCTCCACAGTAAGTGCTGTCAGTGA

Protein-
                                         (SEQ ID NO: 4)
MLESHLIIYFLLAVIQFLLGIFTNGIIVVVNGIDLIKHRKMAPLDLLLSC

LAVSRIFLQLFIFYVNVIVIFFIEFIMCSANCAILLFINELELWLATWLG

VFYCAKVASVRHPLFIWLKMRISKLVPWMILGSLLYVSMICVFHSKYAGF

MVPYFLRKFFSQNATIQKEDTLAIQIFSFVAEFSVPLLIFLFAVLLLIFS

LFRHTRQMRNTVAGSRVPGRGAPISALLSILSFLILYFSHSMIKVFLSSL

KFHIRRFIFLFFILVIGIYPSGHSLILILGNPLKLQNAKKFLLHSKCCQ hT2R67 sequences:
DNA-
                                         (SEQ ID NO: 5)
ATGATAACTTTTCTATACATTTTTTTTCAATTCTAATAATGGTTTTATT

TGTTCTCGGAAACTTTGCCAATGGCTTCATAGCACTGGTAAATTTCATTG

ACTGGGTCAAGAGAAAAAGATCTCCTCACCTGACCAAATTCTCACTGCT

CTGGCGGTCTCCAGAATTGCTTTGCTCTGGGCATTATTATTAAATTGGTA

TTTAACTGTGTTGAATCCAGCTTTTTATAGTGTAGAATTAAGAATTACTT

CTTATAATGCCTGGGTTGTAACCAACCATTTCAGCATGTGGCTTGCTGCT

AACCTCAGCATATTTTATTTGCTCAAGATTGCCAATTTCTCCAACCTTCT

TTTTCTTCATTTAAAGAGGAGAGTTAGGAGTGTCATTCTGGTGATACTGT

TGGGGACTTTGATATTTTTGGTTTGTCATCTTCTTGTGGCAAACATGGAT

GAGAGTATGTGGGCAGAAGAATATGAAGGAAACATGACTGGGAAGATGAA

ATTGAGGAATACAGTACATCTTTCATATTTGACTGTAACTACCCTATGGA

GCTTCATACCCTTTACTCTGTCCCTGATATCTTTTCTGATGCTAATCTGT

TCTCTGTGTAAACATCTCAAGAAGATGCAGCTCCATGGAGAAGGATCGCA

AGATCTCAGCACCAAGGTCCACATAAAAGCTTTGCAAACTCTGATCTCCT

TCCTCTTGTTATGTGCCATTTTCTTTCTATTCCTAATCGTTTCGGTTTGG

AGTCCTAGGAGGCTGCGGAATGACCCGGTTGTCATGGTTAGCAAGGCTGT

TGGAAACATATATCTTGCATTCGACTCATTCATCCTAATTTGGAGAACCA

AGAAGCTAAAACACACCTTTCTTTTGATTTTGTGTCAGATTAGGTGCTGA

Protein-
                                         (SEQ ID NO: 6)
MITFLYIFFSILIMVLFVLGNFANGFIALVNFIDWVKRKKISSADQILTA

LAVSRIGLLWALLLNWYLTVLNPAFYSVELRITSYNAWVVTNHFSMWLAA

NLSIFYLLKIANFSNLLFLHLKRRVRSVILVILLGTLIFLVCHLLVANMD

ESMWAEEYEGNMTGKMKLRNTVHLSYLTVTTLWSFIPFTLSLISFLMLIC

SLCKHLKKMQLHGEGSQDLSTKVHIKALQTLISFLLLCAIFFLFLIVSVW

SPRRLRNDPVVMVSKAVGNIYLAFDSFILIWRTKKLKHTFLLILCQIRC
```

While the foregoing detailed description has described several embodiments of the present invention, it is to be understood that the above description is illustrative only and not limiting of the disclosed invention. The invention is to be limited only by the claims which follow.

---

The invention claimed is:

1. An assay for identifying a compound which blocks or inhibits bitter taste elicited by one or more bitter compounds present in hydrolyzed soy protein by the activation of a human T2R bitter taste receptor comprising:
   i. screening a compound for its effect on the activation of at least one bitter taste receptor polypeptide by hydrolyzed soy protein containing composition wherein said bitter taste receptor polypeptide comprises a polypeptide that is at least 90% identical to SEQ ID NO:6 or to the extracellular or transmembrane region thereof, and
   ii. determining whether said compound modulates bitter taste elicited by said bitter hydrolyzed soy protein containing composition based on whether it has an inhibitory effect on the activation of said receptor by said bitter hydrolyzed soy protein fraction; and
   iii. identifying said compound as a potential bitter taste modulator which potentially may be used as a flavor additive in soy protein containing ingestibles if it inhibits the activation of said human bitter taste receptor by said hydrolyzed soy protein containing composition.

2. The assay of claim 1 wherein said bitter taste receptor polypeptide comprises the sequence in SEQ ID NO:6.

3. The assay of claim 1 wherein said bitter taste receptor polypeptide is expressed on a cell membrane.

4. The assay of claim 1 wherein said bitter taste receptor polypeptide is expressed on an isolated cell membrane.

5. The assay of claim 1 wherein said bitter taste receptor polypeptide is expressed on an intact cell.

6. The assay of claim 1 wherein said bitter taste receptor polypeptide is expressed on a eukaryotic cell.

7. The assay of claim 1 wherein said bitter taste receptor polypeptide is expressed by an amphibian, mammalian or insect cell.

8. The assay of claim 1 wherein said bitter taste receptor polypeptide is expressed on a cell selected from an HEK293, BHK, COS, HEK293T, CHO and Xenopus oocyte.

9. The assay of claim 1 which is a fluorimetric assay.

10. The assay of claim 1 which is a binding assay.

11. The assay of claim 1 which detects the effect of said compound by assaying its effect on an intracellular ion concentration.

12. The assay of claim 1 which detects the effect of said compound on intracellular sodium or calcium.

13. The assay of claim 1 which detects the effect of said compound on cell membrane potential.

14. The assay of claim 1 which detects the effect of said compound on intracellular cAMP, cGMP or IP3.

15. The assay of claim 1 wherein said bitter taste receptor polypeptide comprises only the extracellular region or transmembrane region of said bitter taste receptor polypeptide.

16. The assay of claim 1 wherein said assay detects changes in calcium using a calcium specific fluorescent dye.

17. The assay of claim 1 wherein said assay detects changes in intracellular calcium using a dye selected from Fluo-3, Fluo-4 and Fura-2.

18. The assay of claim 1 wherein said taste receptor is in solution.

19. The assay of claim 1 which is a binding assay that detects changes in spectroscopic characteristics, hydrodynamic characteristics or solubility.

20. The assay of claim 1 which detects the effect of said compound on the complexing of said bitter taste receptor polypeptide with a G protein.

21. The assay of claim 1 which detects the effect of said compound on the complexing of said taste receptor with a G protein selected from transducin, gustducin, Galpha15, Galpha16, or a chimera thereof.

22. The assay of claim 1 which is a fluorescence polarization assay.

23. The assay of claim 1 wherein said bitter taste receptor polypeptide is attached to a solid phase substrate.

24. The assay of claim 1 which is a high throughput assay.

25. The assay of claim 1 wherein the bitter taste receptor polypeptide is expressed by a HEK293 cell.

* * * * *

SEQUENCE LISTING

```
<160> NUMBER OF SEQ ID NOS: 6

<210> SEQ ID NO 1
<211> LENGTH: 35
<212> TYPE: PRT
<213> ORGANISM: HOMO SAPIENS

<400> SEQUENCE: 1

Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30

Glu Pro Trp
        35

<210> SEQ ID NO 2
<211> LENGTH: 374
<212> TYPE: PRT
<213> ORGANISM: HOMO SAPIENS

<400> SEQUENCE: 2

Met Ala Arg Ser Leu Thr Trp Arg Cys Cys Pro Trp Cys Leu Thr Glu
1               5                   10                  15
```

```
Asp Glu Lys Ala Ala Arg Val Asp Gln Glu Ile Asn Arg Ile Leu
            20                  25                  30

Leu Glu Gln Lys Lys Gln Asp Arg Gly Glu Leu Lys Leu Leu Leu
        35                  40                  45

Gly Pro Gly Glu Ser Gly Lys Ser Thr Phe Ile Lys Gln Met Arg Ile
50                  55                  60

Ile His Gly Ala Gly Tyr Ser Glu Glu Glu Arg Lys Gly Phe Arg Pro
65                  70                  75                  80

Leu Val Tyr Gln Asn Ile Phe Val Ser Met Arg Ala Met Ile Glu Ala
                85                  90                  95

Met Glu Arg Leu Gln Ile Pro Phe Ser Arg Pro Glu Ser Lys His His
            100                 105                 110

Ala Ser Leu Val Met Ser Gln Asp Pro Tyr Lys Val Thr Thr Phe Glu
        115                 120                 125

Lys Arg Tyr Ala Ala Ala Met Gln Trp Leu Trp Arg Asp Ala Gly Ile
130                 135                 140

Arg Ala Cys Tyr Glu Arg Arg Arg Glu Phe His Leu Leu Asp Ser Ala
145                 150                 155                 160

Val Tyr Tyr Leu Ser His Leu Glu Arg Ile Thr Glu Glu Gly Tyr Val
                165                 170                 175

Pro Thr Ala Gln Asp Val Leu Arg Ser Arg Met Pro Thr Thr Gly Ile
            180                 185                 190

Asn Glu Tyr Cys Phe Ser Val Gln Lys Thr Asn Leu Arg Ile Val Asp
        195                 200                 205

Val Gly Gly Gln Lys Ser Glu Arg Lys Lys Trp Ile His Cys Phe Glu
210                 215                 220

Asn Val Ile Ala Leu Ile Tyr Leu Ala Ser Leu Ser Glu Tyr Asp Gln
225                 230                 235                 240

Cys Leu Glu Glu Asn Asn Gln Glu Asn Arg Met Lys Glu Ser Leu Ala
                245                 250                 255

Leu Phe Gly Thr Ile Leu Glu Leu Pro Trp Phe Lys Ser Thr Ser Val
            260                 265                 270

Ile Leu Phe Leu Asn Lys Thr Asp Ile Leu Glu Glu Lys Ile Pro Thr
        275                 280                 285

Ser His Leu Ala Thr Tyr Phe Pro Ser Phe Gln Gly Pro Lys Gln Asp
290                 295                 300

Ala Glu Ala Ala Lys Arg Phe Ile Leu Asp Met Tyr Thr Arg Met Tyr
305                 310                 315                 320

Thr Gly Cys Val Asp Gly Pro Glu Gly Ser Asn Leu Lys Lys Glu Asp
                325                 330                 335

Lys Glu Ile Tyr Ser His Met Thr Cys Ala Thr Asp Thr Gln Asn Val
            340                 345                 350

Lys Phe Val Phe Asp Ala Val Thr Asp Ile Ile Lys Glu Asn Leu
        355                 360                 365

Lys Asp Cys Gly Leu Phe
370

<210> SEQ ID NO 3
<211> LENGTH: 900
<212> TYPE: DNA
<213> ORGANISM: HOMO SAPIENS

<400> SEQUENCE: 3
atgctagagt ctcacctcat tatctatttt cttcttgcag tgatacaatt tcttcttggg      60
```

-continued

```
attttcacaa atggcatcat tgtggtggtg aatggcattg acttgatcaa gcacagaaaa    120
atggctccgc tggatctcct tctttcttgt ctggcagttt ctagaatttt tctgcagttg    180
ttcatcttct acgttaatgt gattgttatc ttcttcatag aattcatcat gtgttctgcg    240
aattgtgcaa ttctcttatt tatcaatgaa ttggaacttt ggcttgccac atggctcggc    300
gttttctatt gtgccaaggt tgccagcgtc cgtcacccac tcttcatctg gttgaagatg    360
aggatatcca agctggtccc atggatgatc ctggggtctc tgctatatgt atctatgatt    420
tgtgttttcc atagcaaata tgcagggttt atggtcccat acttcctaag gaaattttc     480
tcccaaaatg ccacaattca aaagaagat acactggcta tacagatttt ctcttttgtt     540
gctgagttct cagtgccatt gcttatcttc cttttgctg ttttgctctt gattttctct     600
ctggggaggc acaccggca atgagaaac acagtggccg gcagcagggt tcctggcagg     660
ggtgcaccca tcagcgcgtt gctgtctatc ctgtccttcc tgatcctcta cttctcccac    720
tgcatgataa aagttttctc tcttctcta agtttcaca tcagaaggtt catctttctg      780
ttcttcatcc ttgtgattgg tatataccct tctggacact ctctcatctt aattttagga    840
aatcctaaat tgaaacaaaa tgcaaaaaag ttcctcctcc acagtaagtg ctgtcagtga    900
```

<210> SEQ ID NO 4
<211> LENGTH: 299
<212> TYPE: PRT
<213> ORGANISM: HOMO SAPIENS

<400> SEQUENCE: 4

```
Met Leu Glu Ser His Leu Ile Ile Tyr Phe Leu Leu Ala Val Ile Gln
1               5                   10                  15

Phe Leu Leu Gly Ile Phe Thr Asn Gly Ile Ile Val Val Val Asn Gly
            20                  25                  30

Ile Asp Leu Ile Lys His Arg Lys Met Ala Pro Leu Asp Leu Leu Leu
        35                  40                  45

Ser Cys Leu Ala Val Ser Arg Ile Phe Leu Gln Leu Phe Ile Phe Tyr
    50                  55                  60

Val Asn Val Ile Val Phe Phe Ile Glu Phe Ile Met Cys Ser Ala
65                  70                  75                  80

Asn Cys Ala Ile Leu Leu Phe Ile Asn Glu Leu Glu Leu Trp Leu Ala
                85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
        115                 120                 125

Met Ile Leu Gly Ser Leu Leu Tyr Val Ser Met Ile Cys Val Phe His
    130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
    210                 215                 220

Ser Ala Leu Leu Ser Ile Leu Ser Phe Leu Ile Leu Tyr Phe Ser His
```

```
                    225                 230                 235                 240

Cys Met Ile Lys Val Phe Leu Ser Ser Leu Lys Phe His Ile Arg Arg
                245                 250                 255

Phe Ile Phe Leu Phe Phe Ile Leu Val Ile Gly Ile Tyr Pro Ser Gly
                260                 265                 270

His Ser Leu Ile Leu Ile Leu Gly Asn Pro Lys Leu Lys Gln Asn Ala
            275                 280                 285

Lys Lys Phe Leu Leu His Ser Lys Cys Cys Gln
        290                 295
```

<210> SEQ ID NO 5
<211> LENGTH: 900
<212> TYPE: DNA
<213> ORGANISM: HOMO SAPIENS

<400> SEQUENCE: 5

```
atgataactt tctatacat tttttttca attctaataa tggttttatt tgttctcgga      60
aactttgcca atggcttcat agcactggta aatttcattg actgggtgaa gagaaaaaag    120
atctcctcag ctgaccaaat tctcactgct ctggcggtct ccagaattgg tttgctctgg    180
gcattattat taaattggta tttaactgtg ttgaatccag cttttttatag tgtagaatta    240
agaattactt cttataatgc ctgggttgta accaaccatt tcagcatgtg gcttgctgct    300
aacctcagca tattttattt gctcaagatt gccaatttct ccaaccttct ttttcttcat    360
ttaaagagga gagttaggag tgtcattctg gtgatactgt tggggacttt gatattttg     420
gtttgtcatc ttcttgtggc aaacatggat gagagtatgt gggcagaaga atatgaagga    480
aacatgactg ggaagatgaa attgaggaat acagtacatc tttcatattt gactgtaact    540
acccctatgga gcttcatacc ctttactctg tccctgatat cttttctgat gctaatctgt    600
tctctgtgta acatctcaa gaagatgcag ctccatggag aaggatcgca agatctcagc    660
accaaggtcc acataaaagc tttgcaaact ctgatctcct tcctcttgtt atgtgccatt    720
ttctttctat tcctaatcgt ttcggtttgg agtcctagga ggctgcggaa tgacccggtt    780
gtcatggtta gcaaggctgt tggaaacata tatcttgcat tcgactcatt catcctaatt    840
tggagaacca agaagctaaa acacaccttt cttttgattt tgtgtcagat taggtgctga    900
```

<210> SEQ ID NO 6
<211> LENGTH: 299
<212> TYPE: PRT
<213> ORGANISM: HOMO SAPIENS

<400> SEQUENCE: 6

```
Met Ile Thr Phe Leu Tyr Ile Phe Phe Ser Ile Leu Ile Met Val Leu
1               5                   10                  15

Phe Val Leu Gly Asn Phe Ala Asn Gly Phe Ile Ala Leu Val Asn Phe
                20                  25                  30

Ile Asp Trp Val Lys Arg Lys Ile Ser Ser Ala Asp Gln Ile Leu
            35                  40                  45

Thr Ala Leu Ala Val Ser Arg Ile Gly Leu Leu Trp Ala Leu Leu
        50                  55                  60

Asn Trp Tyr Leu Thr Val Leu Asn Pro Ala Phe Tyr Ser Val Glu Leu
65                  70                  75                  80

Arg Ile Thr Ser Tyr Asn Ala Trp Val Val Thr Asn His Phe Ser Met
                85                  90                  95

Trp Leu Ala Ala Asn Leu Ser Ile Phe Tyr Leu Leu Lys Ile Ala Asn
```

-continued

```
                    100                 105                 110
Phe Ser Asn Leu Leu Phe Leu His Leu Lys Arg Arg Val Arg Ser Val
        115                 120                 125

Ile Leu Val Ile Leu Leu Gly Thr Leu Ile Phe Leu Val Cys His Leu
        130                 135                 140

Leu Val Ala Asn Met Asp Glu Ser Met Trp Ala Glu Glu Tyr Glu Gly
145                 150                 155                 160

Asn Met Thr Gly Lys Met Lys Leu Arg Asn Thr Val His Leu Ser Tyr
                165                 170                 175

Leu Thr Val Thr Thr Leu Trp Ser Phe Ile Pro Phe Thr Leu Ser Leu
            180                 185                 190

Ile Ser Phe Leu Met Leu Ile Cys Ser Leu Cys Lys His Leu Lys Lys
        195                 200                 205

Met Gln Leu His Gly Glu Gly Ser Gln Asp Leu Ser Thr Lys Val His
        210                 215                 220

Ile Lys Ala Leu Gln Thr Leu Ile Ser Phe Leu Leu Cys Ala Ile
225                 230                 235                 240

Phe Phe Leu Phe Leu Ile Val Ser Val Trp Ser Pro Arg Arg Leu Arg
            245                 250                 255

Asn Asp Pro Val Val Met Val Ser Lys Ala Val Gly Asn Ile Tyr Leu
            260                 265                 270

Ala Phe Asp Ser Phe Ile Leu Ile Trp Arg Thr Lys Lys Leu Lys His
        275                 280                 285

Thr Phe Leu Leu Ile Leu Cys Gln Ile Arg Cys
        290                 295
```